(12) United States Patent
Panda

(10) Patent No.: US 11,850,220 B2
(45) Date of Patent: Dec. 26, 2023

(54) SYNTHESIS OF IBUPROFEN HYBRID CONJUGATES AS ANTI-INFLAMMATORY AND ANALGESIC AGENTS

(71) Applicant: Augusta University Research Institute, Inc., Augusta, GA (US)

(72) Inventor: Siva Panda, Augusta, GA (US)

(73) Assignee: AUGUSTA UNIVERSITY RESEARCH INSTITUTE, INC., Augusta, GA (US)

(*) Notice: Subject to any disclaimer, the term of this patent is extended or adjusted under 35 U.S.C. 154(b) by 6 days.

(21) Appl. No.: 17/324,258

(22) Filed: May 19, 2021

(65) Prior Publication Data
US 2021/0361597 A1 Nov. 25, 2021

Related U.S. Application Data

(60) Provisional application No. 63/027,081, filed on May 19, 2020.

(51) Int. Cl.
| | | |
|---|---|---|
| *A61K 31/165* | (2006.01) | |
| *A61K 47/54* | (2017.01) | |
| *A61P 29/00* | (2006.01) | |
| *A61K 31/167* | (2006.01) | |

(52) U.S. Cl.
CPC .......... *A61K 31/165* (2013.01); *A61K 31/167* (2013.01); *A61K 47/542* (2017.08); *A61P 29/00* (2018.01)

(58) Field of Classification Search
CPC .. A61K 31/165; A61K 47/542; A61K 31/167; A61P 29/00
See application file for complete search history.

(56) References Cited

U.S. PATENT DOCUMENTS

| | | | |
|---|---|---|---|
| 5,948,433 A | 9/1999 | Burton et al. | |
| 5,985,311 A | 11/1999 | Cordes et al. | |
| 6,461,644 B1 | 10/2002 | Jackson et al. | |
| 6,676,961 B1 | 1/2004 | Lichter | |

FOREIGN PATENT DOCUMENTS

| | | | |
|---|---|---|---|
| WO | WO-0158852 A2 * | 8/2001 | ............... A61P 1/04 |
| WO | 2015/120287 A2 | 8/2015 | |

OTHER PUBLICATIONS

Encyclopaedia Britannica (https://www.britannica.com/science/amino-acid, obtained from the internet May 10, 2019) (Year: 2019).*
Sheth et al (J Chem Pharm Res, 2010; 2(2):1-12) (Year: 2010).*

(Continued)

*Primary Examiner* — Rayna Rodriguez
(74) *Attorney, Agent, or Firm* — Smith, Gambrell & Russell; Judy Jarecki-Black

(57) ABSTRACT

Disclosed herein as ibuprofen hybrid conjugates and methods of their use to reduce inflammation, pain, and fever. The ibuprofen conjugates have potent anti-inflammatory and analgesic properties with low potential for ulcerogenic activity. An exemplary compound is an ibuprofen-amino acid-4-aminophenol hybrid. Also disclosed are methods of treating or reducing inflammation, pain, and fever in a subject.

15 Claims, 3 Drawing Sheets

(56) References Cited

OTHER PUBLICATIONS

Abdellatif, K.R.A., et al., "Synthesis, cyclooxygenase inhibition and anti-inflammatory evaluation of new 1,3,5-triaryl-4,5-dihydro-1H-pyrazole derivatives possessing methanesulphonyl pharmacophore", J. Enzyme Inhib. Med. Chem., 31: 1545-1555 (2016).

Allison, M.C., et al., "Gastrointestinal Damage Associated with the Use of Nonsteroidal Antiinflammatory Drugs", New Engl. J. Med., 327: 749-754 (1992).

Amin, K.M., et al., "Synthesis, analgesic and anti-inflammatory activities evaluation of some bi-, tri- and tetracyclic condensed pyrimidines", Eur. J. Med. Chem., 44: 4572-4584 (2009).

Cioli, V., et al., "The role of direct tissue contact in the production of gastrointestinal ulcers by anti-inflammatory drugs in rats", Toxicol. Appl. Pharmacol., 50: 283-289 (1979).

Dannhardt, G., et al., "Structural Approaches to Explain the Selectivity of COX-2 Inhibitors: Is There a Common Pharmacophore?", Curr. Med. Chem., 7(11): 1101-1112 (2000).

Eddy, N.B., et al., "Synthetic Analgesics. II. Dithienylbutenyl- and DithienylButlamines", J. Pharmacol. Exp. Ther., 107(3): 385-393 (1953).

Fox, D.J., et al., "Highly Potent, Orally Available Anti-inflammatory Broad-Spectrum Chemokine Inhibitors", J. Med. Chem., 52(11): 3591-3595 (2009).

Fox, L.T., et al., "Transdermal Drug Delivery Enhancement by Compounds of Natural Origin", Molecules, 16(12): 10507-10540 (2011).

Geronikaki, A.A., et al., "Computer-Aided Discovery of Anti-Inflammatory Thiazolidinones with Dual Cyclooxygenase/Lipoxygenase Inhibition", J. Med. Chem., 51(6): 1601-1609 (2008).

Girgis, A.S., et al., "Computer-assisted rational design, synthesis, and bioassay of non-steroidal anti-inflammatory agents", Eur. J. Med. Chem., 50: 1-8 (2012).

Huang, Z., et al., "Ethanesulfohydroxamic Acid Ester Prodrugs of Nonsteroidal Anti-inflammatory Drugs (NSAIDs): Synthesis, Nitric oxide and Nitroxyl Release, Cyclooxygenase Inhibition, Anti-inflammatory, and Ulcerogenicity Index Studies", J. Med. Chem., 54(5): 1356-1364 (2011).

Husain, A., "Fenbufen based 3-[5-(substituted aryl)-1,3,4-oxadiazol-2-yl]-1-(biphenyl-4-yl)propan-1-ones as safer antiinflammatory and analgesic agents", et al., Eur. J. Med. Chem., 44(9): 3798-3804 (2009).

Kucukguzel, S.G., et al., "Synthesis and Characterization of Celecoxib Derivatives as Possible Anti-Inflammatory, Analgesic, Antioxidant, Anticancer and Anti-HCV Agents", Molecules, 18: 3595-3614 (2013).

Naumov, R.N. et al., "Synthesis and QSAR study of novel anti-in? ammatory activemesalazine-metronidazole conjugates", Bioorg. Med. Chem. Lett., 25: 2314-2320 (2015).

Ozdemir, A., et al., "Synthesis and evaluation of new indole-based chalcones as potential antiinflammatory agents", Eur. J. Med. Chem., 89: 304-309 (2015).

Palomer, et al., "Identification of Novel Cyclooxygenase-2 Selective Inhibitors Using Pharmacophore Models", J. Med. Chem., 45(7): 1402-1411 (2002).

Pathan, I.B.., et al., "Chemical Penetration Enhancers for Transdermal Drug Delivery Systems", Tropical Journal of Pharmaceutical Research, 8(2): 173-179 (2009).

Rayar, A.M., et al., "New selective cyclooxygenase-2 inhibitors from cyclocoumarol: Synthesis, characterization, biological evaluation and molecular modeling", Eur. J. Med. Chem. , 146: 577-587 (2018).

Roubille, C., et al., "Cardiovascular Adverse Effects of Anti-Inflammatory Drugs", Antiinflamm Antiallergy Agents Med. Chem., 12(1): 55-67 (2013).

Sahu, S., et al., "NSAID Conjugates with Carnosine and Amino Acids", Synthesis, 45(24): 3369-3374 (2013).

Sarigol, D., et al., "Novel thiazolo[3,2-b]-1,2,4-triazoles derived from naproxen with analgesic/anti-inflammatory properties: Synthesis, biological evaluation and molecular modeling studies", Bioorg. Med. Chem., 23(10): 2518-2528 (2015).

Tiwari, A.D. et al., "Microwave assisted synthesis and QSAR study of novel NSAID acetaminophen conjugates with amino acid linkers", Org. Biomol. Chem., 12: 7238-7249 (2014).

Turunen, J.H.O., et al., "Frequent analgesic use at population level: Prevalence and patterns of use", Pain, 115(3): 374-381 (2005).

* cited by examiner

SYNTHESIS OF IBUPROFEN HYBRID CONJUGATES AS ANTI-INFLAMMATORY AND ANALGESIC AGENTS

CROSS-REFERENCE TO RELATED APPLICATIONS

This application claims priority to and benefit of U.S. Provisional Patent Application No. 63/027,081 filed on May 19, 2020, and which is incorporated by reference in its entirety.

TECHNICAL FIELD OF THE INVENTION

Aspects of the invention are generally related to anti-inflammatory and analgesic compositions and methods of their use.

BACKGROUND OF THE INVENTION

Inflammation is a component of innate immunity and is a very common response to harmful pathogens or damaged cells. Non-steroidal anti-inflammatory drugs (NSAIDs) that mainly act by cyclooxygenase inhibition are a major drug class. Due to their ample therapeutic use, that ranges from the treatment of fever, inflammation and mild pain up to severe chronic inflammatory disorders (Sorbera, et al., *Drugs Future* 2001, 26, 133-140; Palomer, et al., *J. Med. Chem.* 2002, 45, 1402-1411). NSAIDs, such as ibuprofen, diclofenac, mefenamic acid, indomethacin, and naproxen, are the most commonly prescribed medications (FIG. 1). The long-term use of these NSAIDs may also lead to severe gastrointestinal (GI) damage and renal dysfunction, which limits the use of these drugs (Allison, et al., *New Engl. J. Med.* 1992, 327, 749-754; Cioli, V., et al., *Toxicol. Appl. Pharmacol.* 1979, 50, 283-289; Husain, A., et al., *Eur. J. Med. Chem.* 2009, 44, 3798-3804). The adverse effects are due to the reduction of the levels of protective prostaglandins in the GI tract due to the inhibition of COX-1 (cyclooxygenase-1). Although selective COX-2 inhibitors such as celecoxib, developed and marketed by Pfizer cause less GI adverse effects than non-selective NSAIDs, their use in the treatment is also limited due to their serious cardiovascular effects and renal failure (Turunen, J. H. O., et al., *Pain* 2005, 115, 374-381; Dannhardt, G., et al., *Curr. Med. Chem.* 2000, 7, 1101-1112; Roubille, C., et al., *Antiinflamm Antiallergy Agents Med. Chem.* 2013, 12(1), 55-67; Ozdemit, A., et al., *Eur. J. Med. Chem.* 2015, 89, 304-309). Ideally, anti-inflammatory drugs should only affect uncontrolled inflammation, without interfering with the body's natural immune response. This is one of the body's first line of defense and must not be compromised.

The development of a completely selective NSAID is still a long-standing medicinal chemistry problem and needs to be addressed. Several approaches have been adopted by the medicinal chemistry community to overcome the problem (Huang, Z., et al., *J. Med. Chem.* 2011, 54, 1356-1364; Fox, et al., *J. Med. Chem.* 2009, 52, 3591-3595; Geronikaki, A. A., et al., *J. Med. Chem.* 2008, 51, 1601-1609).

Alternatively, acetaminophen available in the market under the name Tylenol is used as a safer medication for mild pain fever, especially for pregnant women and kids because of its comparative GI safety and its low acquisition costs. Physicians also preferred to prescribe acetaminophen along with ibuprofen (market under the name Motrin) to avoid the associated side effects.

Therefore, it is an object of the invention to provide a safer, more efficacious compositions for treating pain and inflammation in a subject.

SUMMARY OF THE INVENTION

There is a growing need for safer, more tolerable therapeutic agents for inflammatory conditions. Chronic use of current therapeutics can lead to severe gastrointestinal (GI) damage and renal dysfunction. Disclosed herein are ibuprofen hybrid conjugates having anti-inflammatory and analgesic activities with little to no ulcerogenic effects.

One embodiment provides a ibuprofen hybrid conjugate has the general structure according to formula (I):

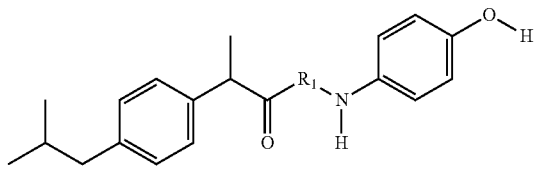

Formula I wherein, $R_1$ can be can be one or more amino acids or salts thereof, nucleic acids, lipids, polysaccharides, polymers, substituted or unsubstituted alkyl groups, alkenyl groups, alkynyl groups, aryl groups, heteroaryl groups, or other organic groups containing between $C_1$ and $C_{30}$ carbon atoms; or an enantiomer, tautomer, stereoisomers, solvate, zwitterion, polymorph, prodrug, or a pharmaceutically acceptable salt thereof.

In some embodiments, $R_1$ is an amino acid. Amino acids include, but not limited to, Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). The amino acid can be an α-amino acid. The amino acid can be a branched chain amino acid.

In another embodiment, the ibuprofen hybrid conjugate has a general structure according to Formula II:

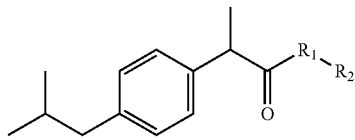

Formula 2 wherein $R_1$ can be one or more amino acids or salts thereof, nucleic acids, lipids, polysaccharides, polymers, substituted or unsubstituted alkyl groups, alkenyl groups, alkynyl groups, aryl groups, heteroaryl groups, or other organic groups containing between $C_1$ and $C_{30}$ carbon atoms; and $R_2$ can be absent or H, substituted or unsubstituted hydroxyl groups, amino groups, alkyl groups, cycloalkyl groups, or aryl groups; or an enantiomer, tautomer, stereoisomers, solvate, zwitterion, polymorph, prodrug, or a pharmaceutically acceptable salt thereof.

In some embodiments, $R_2$ is a substituted or unsubstituted aryl group. In one embodiment, the aryl group is 4-aminophenol.

Another embodiment provides a pharmaceutical composition including an effective amount of at least one of the disclosed ibuprofen hybrid conjugates according to Formula I or II, and optionally a pharmaceutically acceptable excipient. The pharmaceutical compositions can be formulated for oral or parenteral administration.

Another embodiment provides a method of treating inflammation in a subject in need thereof, by administering to the subject a pharmaceutical composition including one or more of the disclosed ibuprofen hybrid conjugates according to Formula I or Formula II in an amount effective to reduce inflammation. The pharmaceutical composition reduces or eliminates one or more symptom of inflammation such as tissue heat, pain, redness, swelling, or loss of function.

Also disclosed is a method of reducing pain in a subject in need thereof by administering to the subject a pharmaceutical composition including one or more of the disclosed ibuprofen hybrid conjugates according to Formula I or Formula II in an amount effective to reduce pain. The pain can be caused by appendicitis, arthritis, bone fracture or break, burns, cancer, central pain, congenital conditions such as curvature of the spine, chronic or acute pain, cluster headaches, crash injury, dental pain, fibromyalgia, gallbladder disease, gastrointestinal disorders, headaches, herpes neuralgia, improper lifting techniques, infection, inflammatory disease, joint damage, lower back pain, menstruation, migraines, multiple sclerosis, nerve damage, neuropathic pain, a non-inflammatory neuropathic or dysfunctional pain condition, nociceptive pain, opioid resistant pain, osteoarthritis, pain during labor and delivery, pain syndromes, phantom limb pain, poor posture, post-operative pain, rheumatoid arthritis, sprains, spinal cord injury, strains, surgery, trauma, toothache, visceral pain, or wound cleansing and debridement.

Yet another embodiment provides a method of reducing or eliminating fever in a subject in need thereof by administering to the subject a pharmaceutical composition including one or more of the disclosed ibuprofen hybrid conjugates according to Formula I or Formula II in an amount effective to reduce fever.

DETAILED DESCRIPTION OF THE INVENTION

I. Definitions

Figure 1A:
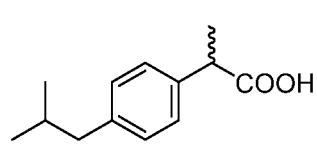
FIGS. 1A-F show chemical structures of common non-steroidal anti-inflammatory drugs (NSAIDs), that are commercially available, including Ibuprofen (FIG. 1A), Diclofenac (FIG. 1B), Mefenamic Acid (FIG. 1C), Indomethacin (FIG. 1D), Naproxen (FIG. 1E), and Acetaminophen (FIG. 1F).
Figure 1B:
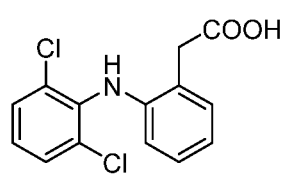
Figure 1C:
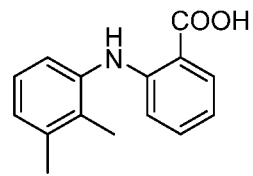
Figure 1D:
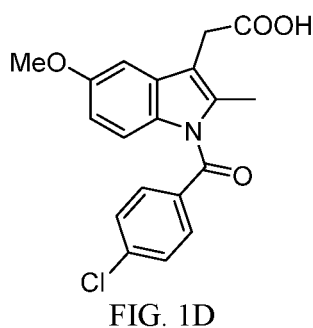
Figure 1E:
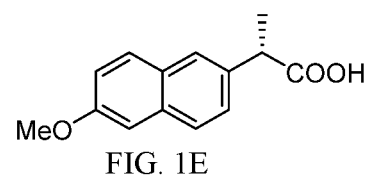
Figure 1F:
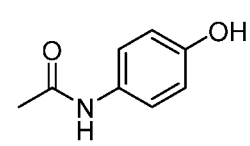

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term, "alkyl," as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycicoalkenyl, cycloalkynyl groups, alkyl substituted cycloalkyl, cycicoalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone, preferably 20 or fewer, and more preferably 10 or fewer.

The term, "alkyl," also includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —$NR_1R_2$, wherein $R_1$ and $R_2$ are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —$CONR_2$, wherein R is hydrogen, alkyl, or aryl; azide, aralkyl, alkoxyl, imino, phosphonate, phosphinate, silyl, ether, sulfonyl, sulfonamido, heterocyclic, aromatic or heteroaromatic moieties, —$CF_3$; —CN; —$NCOCOCH_2CH_2$; —NCOCOCHCH; —NCS; and combinations thereof.

The terms "alkenyl" and "alkynyl", as used herein, refer to unsaturated aliphatic groups analogous in length and possible substitution to the alkyls described above, but that contain at least one double or triple bond respectively.

The term "aryl" refers to a mono- or multi-cyclic aromatic radical having in the range of 6 up to 30 carbon atoms such as phenyl, naphthyl, tetrahydronapthyl, indanyl, and biphenyl.

The term, "heteroaryl," as used herein, refers to straight or branched chain, or cyclic carbon-containing radicals, or combinations thereof, having 3 to 30 carbon atoms where one or more of the carbon atoms are replaced by heteroatoms. Suitable heteroatoms include, but are not limited to, O, N, Si, P and S, where the nitrogen, phosphorous and sulfur atoms are optionally oxidized, and the nitrogen heteroatom is optionally quaternized. One of the rings may also be aromatic. Examples of heterocyclic and heteroaromatic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

As used herein, the term "carrier" or "excipient" refers to an organic or inorganic ingredient, natural or synthetic inactive ingredient in a formulation, with which one or more active ingredients are combined.

As used herein, the term "pharmaceutically acceptable" means a non-toxic material that does not interfere with the effectiveness of the biological activity of the active ingredients.

As used herein, the term "pharmaceutically acceptable salts" includes acid addition salts or addition salts of free bases. "Pharmaceutically acceptable salts" of the disclosed compounds also include all the possible isomers and their mixtures, and any pharmaceutically acceptable metabolite, bioprecursor and/or pro-drug.

As used herein, the terms "effective amount" or "therapeutically effective amount" means a dosage sufficient to alleviate one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the disease or disorder being treated, as well as the route of administration and the pharmacokinetics of the agent being administered.

As used herein, the term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

As used herein, the terms "individual," "host," "subject," and "patient" are used interchangeably and refer to a mammal, including, but not limited to, humans, rodents, such as mice and rats, and other laboratory animals.

The terms "treat," "treating," or "treatment" refer to alleviating, reducing, or inhibiting one or more symptoms or physiological aspects of a disease, disorder, syndrome, or condition. "Treatment" as used herein covers any treatment of a disease in a subject, and includes: (a) preventing the disease or symptom from occurring in a subject which may be predisposed to the disease or symptom, but has not yet been diagnosed as having it; (b) inhibiting the disease symptom, i.e., arresting its development; or (c) relieving the disease symptom, i.e., causing regression of the disease or symptom.

"Inflammation" as used herein, refers to a protective response of the body's tissues to harmful stimuli such as pathogens, damaged cells, or irritants. It is part of a complex biological response. The function of inflammation is to eliminate the initial cause of cell injury, clear out necrotic cells and tissues damaged from the original insult and the inflammatory process, and initiate tissue repair. The five classical signs of inflammation include heat, pain, redness, swelling, and loss of function.

As used herein "analgesic" refers to drugs used to achieve analgesia, or relief from pain. Analgesic drugs act on the peripheral and central nervous systems. They are distinct from anesthetics, which temporarily affect, and in some instances completely eliminate, sensation. Commonly used analgesics include but are not limited to paracetamol, non-steroidal anti-inflammatory drugs, and opioid drugs.

As used herein, the term "pain" refers a distressing feeling often caused by intense or damaging stimuli. The International Association for the Study of Pain defines pain as an unpleasant sensory and emotional experience associate with actual or potential tissue damage, or described in terms of such damage. Pain as used herein refers to all types of pain, including, but not limited to, appendicitis, arthritis, bone fracture or break, burns, cancer, central pain, congenital conditions such as curvature of the spine, chronic or acute pain, cluster headaches, crash injury, dental pain, fibromyalgia, gallbladder disease, gastrointestinal disorders, headaches, herpes neuralgia, improper lifting techniques, infection, inflammatory disease, joint damage, lower back pain, menstruation, migraines, multiple sclerosis, nerve damage, neuropathic pain, a non-inflammatory neuropathic or dysfunctional pain condition, nociceptive pain, opioid resistant pain, osteoarthritis, pain during labor and delivery, pain syndromes, phantom limb pain, poor posture, post-operative pain, rheumatoid arthritis, sprains, spinal cord injury, strains, surgery, trauma, toothache, visceral pain, wound cleansing and debridement. Levels of pain in a subject can be quantified using standard subjective assay scales of pain including, e.g., the Pain Intensity Visual Analogue Scale or Pain Intensity Categorical Scale. Likewise, levels of "pain relief" can also be quantified by a subjective assay, e.g., Time to Perceptible and Meaningful Pain Relief.

II. Ibuprofen Hybrid Conjugates

Disclosed herein are ibuprofen hybrid conjugates and methods of their use. There is a growing need for safer, more tolerable therapeutic agents for inflammatory conditions. Chronic use of current therapeutics can lead to severe gastrointestinal (GI) damage and renal dysfunction. The disclosed ibuprofen hybrid conjugates have been found to possess potent anti-inflammatory and analgesic activities with a significant reduction in ulcerogenic effects.

Figure 2:
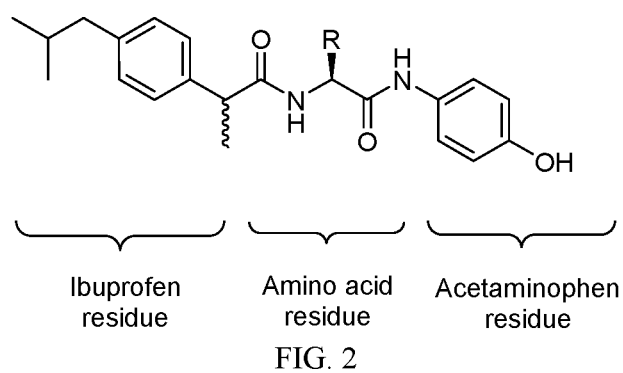
FIG. 2 shows the chemical structure of disclosed representative ibuprofen hybrid conjugate.

In one embodiment, the disclosed ibuprofen hybrid conjugates utilize the carboxylic acid group of ibuprofen in the synthesis of the hybrid conjugates with 4-aminophenol (precursor of acetaminophen) via amino acid as a linker (FIG. 2).

A. Compounds

One embodiment provides a compound according to the following structure:

Formula 1

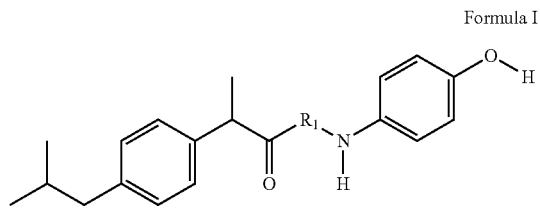

wherein, $R_1$ can be can be one or more amino acids or salts thereof, nucleic acids, lipids, polysaccharides, polymers, substituted or unsubstituted alkyl groups, alkenyl groups, alkynyl groups, aryl groups, heteroaryl groups, or other organic groups containing between $C_1$ and $C_{30}$ carbon atoms; or an enantiomer, tautomer, stereoisomers, solvate, zwitterion, polymorph, prodrug, or a pharmaceutically acceptable salt thereof.

Another embodiment provides a compound according to the following structure:

Formula 2

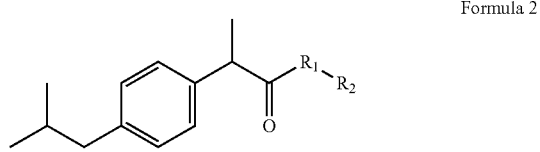

wherein $R_1$ can be one or more amino acids or salts thereof, nucleic acids, lipids, polysaccharides, polymers, substituted or unsubstituted alkyl groups, alkenyl groups, alkynyl groups, aryl groups, heteroaryl groups, or other organic groups containing between $C_1$ and $C_{30}$ carbon atoms; and $R_2$ can be absent or H, substituted or unsubstituted hydroxyl groups, amino groups, alkyl groups, cycloalkyl groups, or aryl groups; or an enantiomer, tautomer, stereoisomers, solvate, zwitterion, polymorph, prodrug, or a pharmaceutically acceptable salt thereof.

In one embodiment, $R_2$ is 4-aminophenol.

1. Ibuprofen

Ibuprofen is a medication in the nonsteroidal anti-inflammatory drug (NSAID) class that is used for treating pain, fever, and inflammation. Chronic used of ibuprofen can lead to side effects such as gastrointestinal bleeding, ulcers, and an increased risk of heart failure, kidney failure, and liver failure. Ibuprofen works by inhibiting the production of prostaglandins by decreasing the activity of the enzyme cyclooxygenase. The structure of ibuprofen is shown in FIG. 1A.

It has been discovered that modifying the carboxylic group of ibuprofen with amino acids, and optionally acetaminophen derivatives, produces a nonsteroidal anti-inflammatory (NSAID) composition having fewer side effects than traditional NSAIDs. Exemplary amino acids that can be used to modify the carboxylic acid of ibroprofen include but are not limited to Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). The carboxylic group of ibuprofen is activated using method known in the art (Tiwari, A. D., et al., *Org Biomol Chem*, 7238-7249 (2014)) to produce a benzotriazolide. The benzotriadolide of ibuprofen is then conjugated with amino acids (one amino acid at a time) in the presence of triethylamine in a mixture of acetonitrile-water to yield ibuprofen-amino acid conjugates. These conjugates can optionally be further coupled with 4-aminophenol (4-AP), or other acetaminophen derivatives, for example in the presence of N-methylmorpholine (NMM) and isobutyl chloroformate (IBCF) in DMF at −5 to 20° C. for 6 h to obtain the ibuprofen-amino acid-4-AP hybrid conjugates.

2. Amino Acid Linker

As discussed above, some of the ibuprofen hybrid conjugates include one or more amino acids. The one or more amino acids can be standard or non-standard amino acids. "Standard amino acid" or "canonical amino acid" typically refers to the twenty amino acids that are encoded directly by the codons of the universal genetic code denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Non-standard amino acid (nsAA)" refers to any and all amino acids that are not a standard amino acid. nsAA can be created by enzymes through posttranslational modifications; or those that are not found in nature and are entirely synthetic (e.g., synthetic amino acids (sAA)). In both classes, the nsAAs can be made synthetically. For example, in some embodiments, a tyrosine residue is substituted for a synthetic tyrosine derivative. WO 2015/120287 provides a non-exhaustive list of exemplary non-standard and synthetic amino acids that are known in the art (see, e.g., Table 11 of WO 2015/120287) and which is incorporated by reference in its entirety.

The amino acid(s) can be "D" amino acid(s), "L" amino acid(s), or a combination thereof. In some embodiments, the composition includes a mixture of ibuprofen hybrid conjugates. In some embodiments the mixture of ibuprofen hybrid conjugates includes one or more conjugate having one or more D amino acids and one or more conjugates having one or more L amino acids. In some embodiments, an ibuprofen hybrid conjugate includes at least one D amino acid and one L amino acid. The D and L amino acids can have the same or different side chains.

In some embodiments, the ibuprofen hybrid conjugates may include a salt form of the amino acid. That is, the one or more amino acids conjugated directly or indirectly to the disclosed ibuprofen hybrid conjugates may include a salt form of the amino acid. For example, the ibuprofen hybrid conjugates may include hydrochloride salt forms of the amino acid. In another embodiment, the ibuprofen hybrid conjugates may include acetate salt forms of the amino acid.

In another embodiment, the ibuprofen hybrid conjugates include α-amino acid analogs, β-amino acid analogs, or combinations thereof. In one embodiment, the amino acid linker is an α-amino acid. In some embodiments, branching of the α-amino acid is a controlling factor governing the anti-inflammatory activity associated with the conjugate.

3. Acetaminophen Derivatives

In some embodiments, the disclosed ibuprofen hybrid conjugates include acetaminophen or an acetaminophen derivative. Paracetamol, also known as acetaminophen and APAP, is a medication used to treat pain and fever. In one embodiment, the acetaminophen derivative is 4-AP. In another embodiment, the disclosed ibuprofen hybrid conjugates include a phenolic derivative of acetaminophen, salicylate, or 5-aminosalicylate (5-ASA).

4. Exemplary Ibuprofen Hybrid Conjugates

It has been discovered that coupling ibuprofen to 4-aminophenol (4AP) with amino acids yields potent hybrid molecules with potent anti-inflammatory and analgesic activities and reduced ulcerogenic effect. To do this, the carboxylic acid group of ibuprofen was utilized in the synthesis of the hybrid conjugates with 4-aminophenol (precursor of acetaminophen) via amino acid as a linker. Optimal reaction conditions were established, which involved utilizing different coupling reagents and solvents at varied temperatures. Once favorable conditions were obtained, several ibuprofen-amino acid conjugates and ibuprofen-amino acid-4AP hybrid conjugates were successfully synthesized in excellent yield. In doing so, an efficient methodology for synthesizing these conjugates was developed. Exemplary ibuprofen hybrid conjugates are illustrated below.

One embodiment provides an ibuprofen hybrid conjugate having a structure according to any one of the following:

(5a)

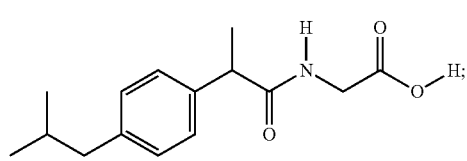

2-(4-Isobutylphenyl)propanoyl)glycine (Ibu-Gly-OH)

(5b)

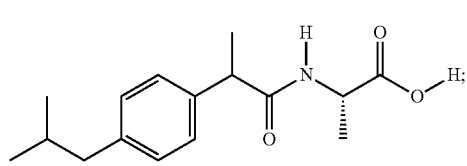

2-(4-Isobutylphenyl)propanoyl)-L-alamine (Ibu-L-Ala-OH)

(5c)

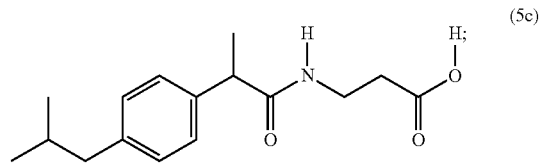

3-(2-(4-Isobutylphenyl)propanamido)propanoic acid (Ibu-β-Ala-OH)

(5d)

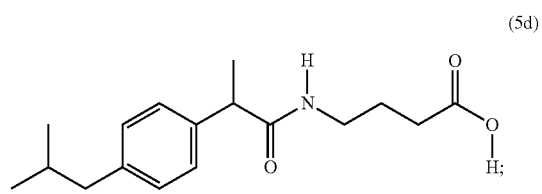

4-(2-(4-Isobutylphenyl)propanamido)butanoic acid (Ibu-GABA-OH)

(5e)

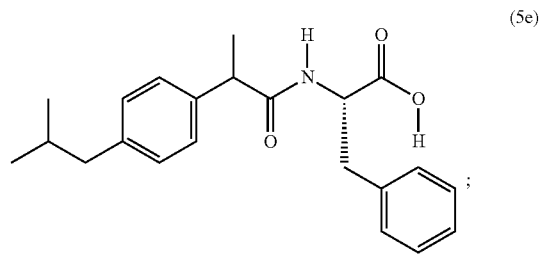 [SMILES: CC(C)Cc1ccc(C(C)C(=O)N[C@@H](Cc2ccccc2)C(=O)O)cc1]

(2-(4-Isobutylphenyl)propanoyl)-L-phenylalanine (Ibu-L-Phe-OH)

(5f)

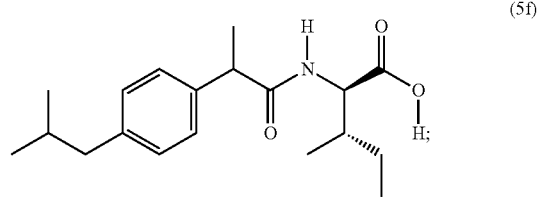

(2-(4-Isobutylphenyl)propanoyl)-L-isoleucine (Ibu-L-Ile-OH)

(5g)

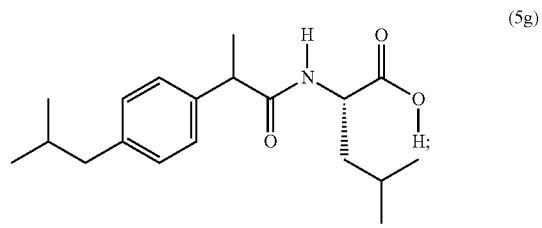

(2-(4-Isobutylphenyl)propanoyl)-L-phenylalanine (Ibu-L-Phe-OH)

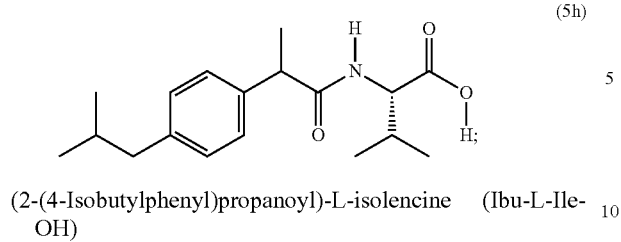

(2-(4-Isobutylphenyl)propanoyl)-L-isolencine (Ibu-L-Ile-OH)

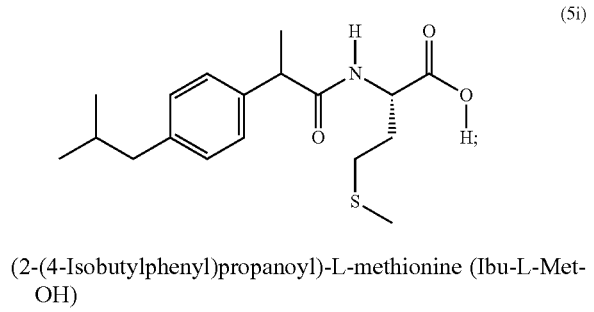

(2-(4-Isobutylphenyl)propanoyl)-L-methionine (Ibu-L-Met-OH)

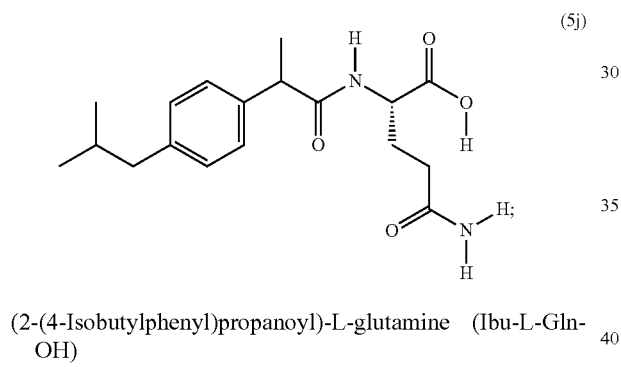

(2-(4-Isobutylphenyl)propanoyl)-L-glutamine (Ibu-L-Gln-OH)

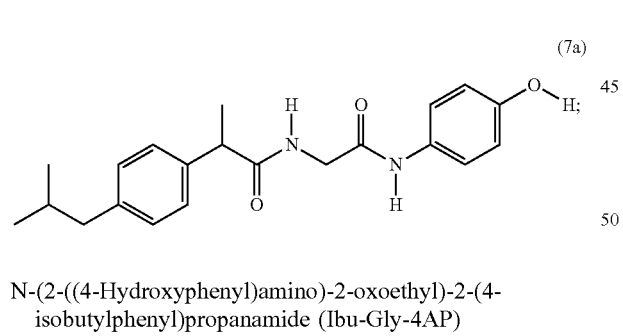

N-(2-((4-Hydroxyphenyl)amino)-2-oxoethyl)-2-(4-isobutylphenyl)propanamide (Ibu-Gly-4AP)

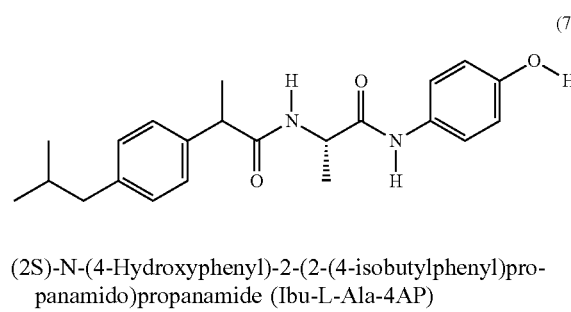

(2S)-N-(4-Hydroxyphenyl)-2-(2-(4-isobutylphenyl)propanamido)propanamide (Ibu-L-Ala-4AP)

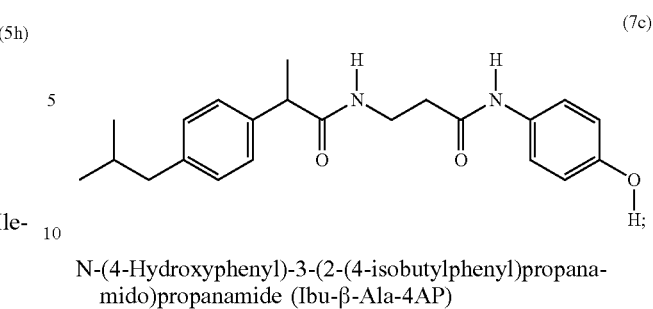

N-(4-Hydroxyphenyl)-3-(2-(4-isobutylphenyl)propanamido)propanamide (Ibu-β-Ala-4AP)

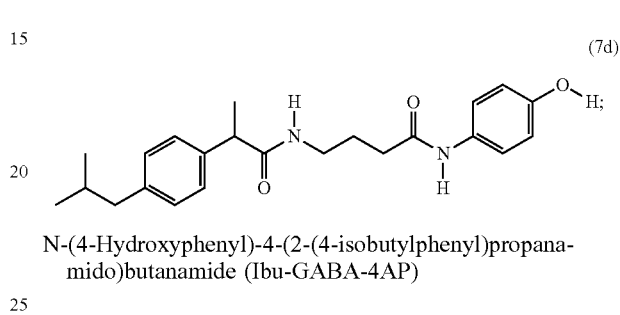

N-(4-Hydroxyphenyl)-4-(2-(4-isobutylphenyl)propanamido)butanamide (Ibu-GABA-4AP)

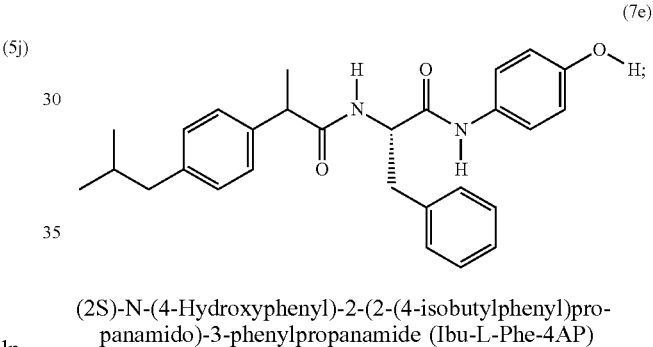

(2S)-N-(4-Hydroxyphenyl)-2-(2-(4-isobutylphenyl)propanamido)-3-phenylpropanamide (Ibu-L-Phe-4AP)

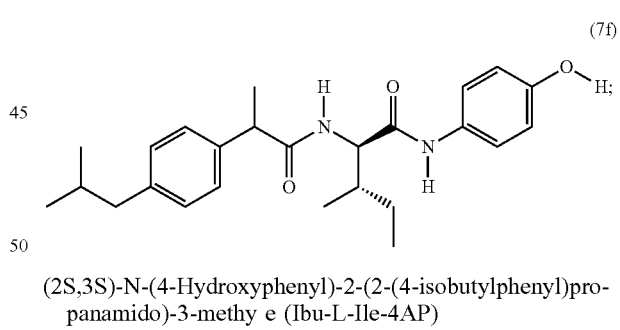

(2S,3S)-N-(4-Hydroxyphenyl)-2-(2-(4-isobutylphenyl)propanamido)-3-methy e (Ibu-L-Ile-4AP)

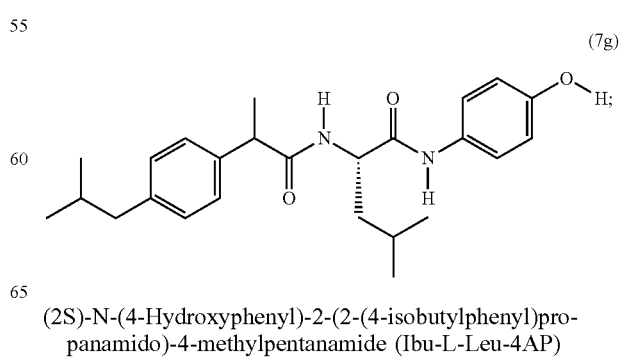

(2S)-N-(4-Hydroxyphenyl)-2-(2-(4-isobutylphenyl)propanamido)-4-methylpentanamide (Ibu-L-Leu-4AP)

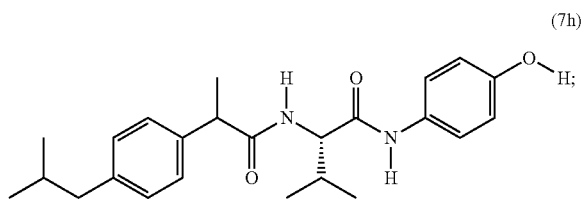

(2S)-N-(4-Hydroxyphenyl)-2-(2-(4-isobutylphenyl)pro-panamido)-3-methylbutanamide (Ibu-L-Val-4AP)

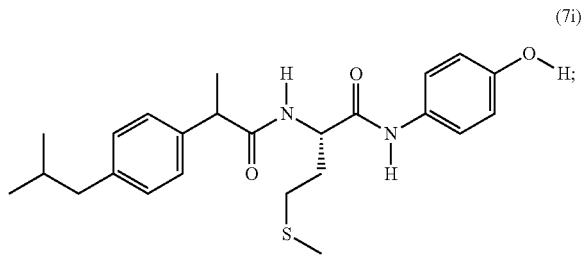

and
(2S)-N-(4-Hydroxyphenyl)-2-(2-(4-isobutylphenyl)pro-panamido)-4-(methylthio)butanamide (Ibu-L-Met-4AP)

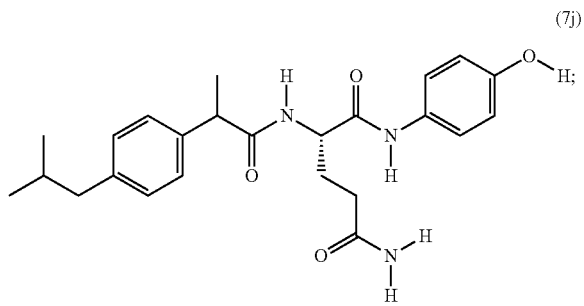

(2S)-N1-(4-Hydroxyphenyl)-2-(2-(4-isobutylphenyl)pro-panamido)pentanediamide (Ibu-L-Gln-4AP)
or a pharmaceutically acceptable salt thereof.

B. Pharmaceutical Compositions

Pharmaceutical compositions including the disclosed ibuprofen hybrid conjugates are provided. In general, pharmaceutical compositions are provided including effective amounts of the disclosed ibuprofen hybrid conjugates, and optionally pharmaceutically acceptable diluents, preservatives, solubilizers, emulsifiers, adjuvants, excipients, and/or carriers. Pharmaceutical compositions can be formulated for administration by parenteral (for example, intramuscular, intraperitoneal, intravitreally, intravenous (IV), or subcutaneous injection), enteral, transmucosal (for example, nasal, vaginal, rectal, or sublingual), or transdermal routes of administration or using bioerodible inserts including ocular inserts and can be formulated in dosage forms appropriate for each route of administration. The compositions can be administered systemically.

The pharmaceutical compositions can be formulated for immediate release, extended release, or modified release. A delayed release dosage form is one that releases a drug (or drugs) at a time other than promptly after administration. An extended release dosage form is one that allows at least a twofold reduction in dosing frequency as compared to that drug presented as a conventional dosage form (e.g. as a solution or prompt drug-releasing, conventional solid dosage form). A modified release dosage form is one for which the drug release characteristics of time course and/or location are chosen to accomplish therapeutic or convenience objectives not offered by conventional dosage forms such as solutions, ointments, or promptly dissolving dosage forms. Delayed release and extended release dosage forms and their combinations are types of modified release dosage forms.

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes, but is not limited to, diluents, binders, lubricants, desintegrators, fillers, and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6$^{th}$ Edition, Ansel et. al., (Media, PA: Williams and Wilkins, 1995) which provides information on carriers, materials, equipment and process for preparing tablets and capsules and delayed release dosage forms of tablets, capsules, and granules.

The compositions can be administered to a subject with or without the aid of a delivery vehicle. Appropriate delivery vehicles for the compounds are known in the art and can be selected to suit the particular active agent. For example, in some embodiments, the active agent(s) is incorporated into or encapsulated by, or bound to, a nanoparticle, microparticle, micelle, synthetic lipoprotein particle, or carbon nanotube. For example, the compositions can be incorporated into a vehicle such as polymeric microparticles which provide controlled release of the active agent(s). In some embodiments, release of the drug(s) is controlled by diffusion of the active agent(s) out of the microparticles and/or degradation of the polymeric particles by hydrolysis and/or enzymatic degradation.

Suitable polymers include ethylcellulose and other natural or synthetic cellulose derivatives. Polymers which are slowly soluble and form a gel in an aqueous environment, such as hydroxypropyl methylcellulose or polyethylene oxide, may also be suitable as materials for drug containing microparticles or particles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof. In some embodiments, both agents are incorporated into the same particles and are formulated for release at different times and/or over different time periods. For example, in some embodiments, one of the agents is released entirely from the particles before release of the second agent begins. In other embodiments, release of the first agent begins followed by release of the second agent before the all of the first agent is released. In still other embodiments, both agents are released at the same time over the same period of time or over different periods of time.

1. Formulations for Parenteral Administration

Compounds and pharmaceutical compositions thereof containing the disclosed conjugates can be administered in an aqueous solution, by parenteral injection. The formulation may also be in the form of a suspension or emulsion. In general, pharmaceutical compositions are provided including effective amounts of the active agent(s) and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as POLYSORBATE® 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

a. Oral Immediate Release Formulations

Suitable oral dosage forms of the disclosed conjugates include tablets, capsules, solutions, suspensions, syrups, and lozenges. Tablets can be made using compression or molding techniques well known in the art. Gelatin or non-gelatin capsules can be prepared as hard or soft capsule shells, which can encapsulate liquid, solid, and semi-solid fill materials, using techniques well known in the art.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydorxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, POLOXAMER® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads granules or particles may also contain minor amount of nontoxic auxiliary substances such as wetting or emulsifying agents, dyes, pH buffering agents, and preservatives.

b. Extended Release Dosage Forms

One embodiment provides an extended release formulation containing one or more of the disclosed conjugates. The extended release formulations are generally prepared as diffusion or osmotic systems, for example, as described in "Remington—The science and practice of pharmacy" (20th ed., Lippincott Williams & Wilkins, Baltimore, MD, 2000). A diffusion system typically consists of two types of devices, reservoir and matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but not limited to, methyl acrylate-methyl methacrylate, polyvinyl chloride, and polyethylene. Hydrophilic polymers include, but are not limited to, methylcellulose, hydroxypropylcellulose, hydroxypropylmethylcellulose, sodium carboxymethylcellulose, and carbopol 934, polyethylene oxides. Fatty compounds include, but are not limited to, various waxes such as carnauba wax and glyceryl tristearate.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above could be combined in a final dosage form comprising single or multiple units. Examples of multiple units include multilayer tablets, capsules containing tablets, beads, granules, etc.

An immediate release portion can be added to the extended release system by means of either applying an immediate release layer on top of the extended release core using coating or compression process or in a multiple unit system such as a capsule containing extended and immediate release beads.

Extended release tablets containing hydrophilic polymers are prepared by techniques commonly known in the art such as direct compression, wet granulation, or dry granulation processes. Their formulations usually incorporate polymers, diluents, binders, and lubricants as well as the active pharmaceutical ingredient. The usual diluents include inert powdered substances such as any of many different kinds of starch, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidine can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In a congealing method, the drug is mixed with a wax material and either spray-congealed or congealed and screened and processed.

c. Delayed Release Dosage Forms

Another embodiment provides a delated release formulation containing one or more of the disclosed conjugates. Delayed release formulations are created by coating a solid dosage form with a film of a polymer which is insoluble in the acid environment of the stomach, and soluble in the neutral environment of small intestines.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT®. (Rohm Pharma; Westerstadt, Germany), including EUDRAGIT®. L30D-55 and L100-55 (soluble at pH 5.5 and above), EUIDRAGIT®. L-100 (soluble at pH 6.0 and above), EUDRAGIT®. S (soluble at pH 7.0 and above, as a result of a higher degree of esterification), and EUIDRAGITS®. NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

2. Formulations for Mucosal and Pulmonary Administration

The disclosed conjugates and compositions thereof can be formulated for pulmonary or mucosal administration. The administration can include delivery of the composition to the lungs, nasal, oral (sublingual, buccal), vaginal, or rectal mucosa. In a particular embodiment, the composition is formulated for and delivered to the subject sublingually.

In one embodiment, the conjugates are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per $cm^3$, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, CA).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different active agents may be administered to target different regions of the lung in one administration.

3. Topical and Transdermal Formulations

Transdermal formulations containing the disclosed conjugates may also be prepared. Delivery of drugs by the transdermal route has been known for many years. Advantages of a transdermal drug delivery compared to other types of medication delivery such as oral, intravenous, intramuscular, etc., include avoidance of hepatic first pass metabolism, ability to discontinue administration by removal of the system, the ability to control drug delivery for a longer time than the usual gastrointestinal transit of oral dosage form, and the ability to modify the properties of the biological barrier to absorption. These will typically be gels, ointments, lotions, sprays, or patches, all of which can be prepared using standard technology. Transdermal formulations can include penetration enhancers.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components.

Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, C12-C15 alkyl benzoates, mineral oil, squalane, cyclomethicone, capric/caprylic triglycerides, and combinations thereof.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

The basic difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

An "oil" is a composition containing at least 95% wt of a lipophilic substance. Examples of lipophilic substances include but are not limited to naturally occurring and synthetic oils, fats, fatty acids, lecithin, triglycerides and combinations thereof.

"Emollients" are an externally applied agent that softens or soothes skin and are generally known in the art and listed in compendia, such as the "Handbook of Pharmaceutical Excipients", $4^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

Additional agents that can be added to the formulation include penetration enhancers. In some embodiments, the penetration enhancer increases the solubility of the drug, improves transdermal delivery of the drug across the skin, in particular across the stratum corneum, or a combination thereof. Some penetration enhancers cause dermal irritation, dermal toxicity and dermal allergies. However, the more commonly used ones include urea, (carbonyldiamide), imidurea, N, N-diethylformamide, N-methyl-2-pyrrolidone, 1-dodecal-azacycloheptane-2-one, calcium thioglycate, 2-pyrrolidone, N,N-diethyl-m-toluamide, oleic acid and its ester derivatives, such as methyl, ethyl, propyl, isopropyl, butyl, vinyl and glycerylmonooleate, sorbitan esters, such as sorbitan monolaurate and sorbitan monooleate, other fatty acid esters such as isopropyl laurate, isopropyl myristate, isopropyl palmitate, diisopropyl adipate, propylene glycol monolaurate, propylene glycol monooleatea and non-ionic detergents such as BRIJ® 76 (stearyl poly(10 oxyethylene ether), BRU® 78 (stearyl poly(20)oxyethylene ether), BRU® 96 (oleyl poly(10)oxyethylene ether), and BRU® 721 (stearyl poly (21) oxyethylene ether) (ICI Americas Inc. Corp.). Chemical penetrations and methods of increasing transdermal drug delivery are described in Inayat, et al., *Tropical Journal of Pharmaceutical Research*, 8(2):173-179 (2009) and Fox, et al., *Molecules*, 16:10507-10540 (2011). In some embodiments, the penetration enhancer is, or includes, an alcohol such ethanol, or others disclosed herein or known in the art.

a. Controlled Release Transdermal Devices

One embodiment provides a controlled release transdermal device containing one or more of the disclosed conjugates. Controlled release transdermal devices rely for their effect on delivery of a known flux of drug to the skin for a prolonged period of time, generally a day, several days, or a week. Two mechanisms are used to regulate the drug flux: either the drug is contained within a drug reservoir, which is separated from the skin of the wearer by a synthetic membrane, through which the drug diffuses; or the drug is held dissolved or suspended in a polymer matrix, through which the drug diffuses to the skin. Devices incorporating a reservoir will deliver a steady drug flux across the membrane as long as excess undissolved drug remains in the reservoir; matrix or monolithic devices are typically characterized by a falling drug flux with time, as the matrix layers closer to the skin are depleted of drug. Usually, reservoir patches include a porous membrane covering the reservoir of medication which can control release, while heat melting thin layers of medication embedded in the polymer matrix (e.g., the adhesive layer), can control release of drug from matrix or monolithic devices. Accordingly, the active agent can be released from a patch in a controlled fashion without necessarily being in a controlled release formulation.

Patches can include a liner which protects the patch during storage and is removed prior to use; drug or drug solution in direct contact with release liner; adhesive which serves to adhere the components of the patch together along with adhering the patch to the skin; one or more membranes, which can separate other layers, control the release of the drug from the reservoir and multi-layer patches, etc., and backing which protects the patch from the outer environment.

Common types of transdermal patches include, but are not limited to, single-layer drug-in-adhesive patches, wherein the adhesive layer contains the drug and serves to adhere the various layers of the patch together, along with the entire system to the skin, but is also responsible for the releasing of the drug; multi-layer drug-in-adhesive, wherein which is similar to a single-layer drug-in-adhesive patch, but contains multiple layers, for example, a layer for immediate release of the drug and another layer for control release of drug from the reservoir; reservoir patches wherein the drug layer is a liquid compartment containing a drug solution or suspension separated by the adhesive layer; matrix patches, wherein a drug layer of a semisolid matrix containing a drug solution or suspension which is surrounded and partially overlaid by the adhesive layer; and vapor patches, wherein an adhesive layer not only serves to adhere the various layers together but also to release vapor. Methods for making transdermal patches are described in U.S. Pat. Nos. 6,461,644, 6,676,961, 5,985,311, and 5,948,433.

In some embodiments, the composition is formulated for transdermal delivery and administered using a transdermal patch. In some embodiments, the formulation, the patch, or both are designed for extended release of the ibuprofen hybrid conjugate.

III. Methods of Use

The disclosed ibuprofen hybrid conjugates are useful as nonsteroidal anti-inflammatory agents and as analgesic agents. The conjugates can be used to treat or prevent inflammation, an inflammatory response, or an autoimmune disorder. One embodiment provides a method of treating inflammation in a subject by administering to the subject a pharmaceutical composition including one or more of the disclosed ibuprofen hybrid conjugates in an amount effective to reduce inflammation in the subject.

Another embodiment provides a method of reducing fever in a subject in need thereof by administering to the subject a pharmaceutical composition including one or more of the disclosed ibuprofen hybrid conjugates in an amount effective to reduce fever in the subject.

In some embodiments, the effect of the composition on a subject is compared to a control. For example, the effect of the composition on a particular symptom, pharmacologic, or physiologic indicator can be compared to an untreated subject, or the condition of the subject prior to treatment. In some embodiments, the symptom, pharmacologic, or physiologic indicator is measured in a subject prior to treatment, and again one or more times after treatment is initiated. In some embodiments, the control is a reference level, or an average determined from measuring the symptom, pharmacologic, or physiologic indicator in one or more subjects that do not have the disease or condition to be treated (for example, healthy subjects). In some embodiments, the effect of the treatment is compared to a conventional treatment that is known in the art. For example, if the disease to be treated is cancer, the conventional treatment could be a chemotherapeutic agent.

Generally, dosage levels, for the compounds disclosed herein are between about 200 mg to 400 mg every 4 hours as needed for adult subjects. The maximum daily recommended dose is 3200 mg/day for an adult subject. In pediatric subjects the compounds are dosed based on weight as follows: weight 12 to 17 pounds (5.45 to 7.73 kg): 50 mg orally every 6 to 8 hours as needed, weight 18 to 23 pounds (8.18 to 10.45 kg): 75 mg orally every 6 to 8 hours as needed. For children from 1 year to 12 years old, a dose of 5 mg/kg to 40 mg/kg every 6 to 8 hours can be administered with a maximum dose of 1200 mg/day.

In some embodiments, one or more of the disclosed ibuprofen hybrid conjugates are used as a pretreatment to another therapy. In some of these embodiments, pretreatment with the disclosed conjugates allows the use of a lower dose of pain reliever or analgesic. In some embodiments, the ibuprofen hybrid conjugate is administered before chemotherapy treatment, radiation treatment, a biopsy, or a blood transfusion. It should be understood that these are non-limiting examples and that the ibuprofen hybrid conjugates described herein can be administered as a pretreatment to any therapy where pain and/or fever are predicted to occur.

In some embodiments, one or more of the disclosed ibuprofen hybrid conjugates is administered to a subject prior to a surgical intervention, e.g., about 4 hours or less prior to the surgical intervention, i.e., about 3 hours, 2 hours, 1 hours, 30 minutes, 15 minutes or even during the surgical intervention itself.

In some embodiments, one or more of the disclosed ibuprofen hybrid conjugates is administered to a subject after undergoing a surgical intervention, e.g., within about 12 hours after a surgical intervention, i.e., within 11 hours, 10 hours, 9 hours, 8 hours, 6 hours, 5 hours, 4 hours, 3 hours, 2 hours, 1 hours, 45 minutes, 30 minutes 15 minutes, 5 minutes, or any period within about 12 hours following a surgical intervention.

A. Methods of Reducing Inflammation

Methods of using the disclosed ibuprofen hybrid conjugates to treat or prevent inflammation in a subject are provided. Methods typically include administering a subject in need thereof an effective amount of a composition including one or more ibuprofen hybrid conjugates.

In one embodiment, the present invention provides methods of treating an inflammatory response and/or an autoimmune disorder in a subject in need thereof. For example, the disclosed methods can be used to prophylactically or therapeutically inhibit, reduce, alleviate, or permanently reverse inflammation of an inflammatory response or autoimmune disorder. In some embodiments, the disclosed compositions are effective in treating chronic inflammation or chronic inflammatory conditions. The term "chronic inflammation" as used herein refers to constantly recurring inflammation or inflammation that lasts for more than three months. An inflammatory response or autoimmune disorder can be inhibited or reduced in a subject by administering to the subject an effective amount of the disclosed compositions.

Administering the composition to a subject can, for example, reduce inflammation in the subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative to the inflammation in an subject not administered the composition. A reduction in inflammation can be measured by a reduction in a molecular manifestation of inflammation, for example, cytokine secretion (e.g., tumor necrosis factor alpha, interferon gamma), or a by a physical manifestation of inflammation, for example, swelling or redness.

In some embodiments, the composition achieves one, two, three, four, or more of the following effects: (i) reduction or amelioration of the severity of an autoimmune or inflammatory disorder or symptom associated therewith; (ii) reduction in the duration of a symptom associated with an autoimmune or inflammatory disorder; (iii) prevention of the progression of an autoimmune or inflammatory disorder, or symptom associated therewith; (iv) regression of an autoimmune or inflammatory disorder, or symptom associated therewith; (v) prevention of the development or onset of a symptom associated with an autoimmune or inflammatory disorder; (vi) prevention of the recurrence of a symptom associated with an autoimmune or inflammatory disorder; (vii) reduction in organ failure associated with an autoimmune or inflammatory disorder; (viii) reduction in the hospitalization of a subject; (ix) reduction in the hospitalization length; (x) an increase in the survival of a subject with an autoimmune or inflammatory disorder; (xi) a reduction in the number of symptoms associated with an autoimmune or inflammatory disorder; (xii) a reduction in inflammation of inflammatory cells; (xiii) a reduction in inflammatory cytokines; (xiv) a reduction in inflammation associated with an autoimmune or inflammatory disorder; (xv) improve life expectancy; (xvi) increase symptom-free survival; (xvii) increase the length of symptom-free remission; and/or (xviii) an enhancement, improvement, supplementation, complementation, or augmentation of the prophylactic or therapeutic effect(s) of another therapy.

Representative inflammatory conditions and autoimmune diseases that can be inhibited or treated by the disclosed compositions include, but are not limited to, rheumatoid arthritis, osteoarthritis, progressive systemic sclerosis, inflammatory bowel disease, idiopathic pulmonary fibrosis, sarcoidosis, hypersensitivity pneumonitis, chronic bronchitis, emphysema, or asthma, pelvic inflammatory disease, Legionella, Lyme disease, Influenza A, Epstein-Barr virus, encephalitis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Bechet's disease, bullous pemphigoid, cardiomyopathy, celiac sprue-dermatitis, chronic fatigue syndrome immune deficiency, syndrome (CFIDS), chronic inflammatory demyelinating polyneuropathy, chronic renal failure, chronic kidney disease, cicatricial pemphigoid, cold agglutinin disease, Crest syndrome, Crohn's disease, cystic fibrosis, Dego's disease, dermatitis dermatomyositis, dermatomyositis juvenile, discoid lupus, essential mixed cryoglobulinemia, fibromyalgia-fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type 1), Type 2 diabetes, juvenile arthritis, Meniere's disease, mixed connective tissue disease, multiple sclerosis, myasthenia gravis, pancreatitis, pemphigus vulgaris, pernicious anemia, polyarteritis *nodosa*, polychondritis, polyglancular syndromes, polymyalgia rheumatica, polymyositis and dermatomyositis, pneumonia, primary agammaglobulinemia, primary biliary cirrhosis, psoriasis, Raynaud's phenomenon, Reiter's syndrome, rheumatic fever, sarcoidosis, scleroderma, sepsis, septicemia, Sjogren's syndrome, stiff-man syndrome, Takayasu arteritis, temporal arteritis/giant cell arteritis, ulcerative colitis, uveitis, vasculitis, vitiligo, and Wegener's granulomatosis.

In some embodiments, the disclosed ibuprofen hybrid conjugates reduce or eliminate a symptom of inflammation such as heat, pain, redness, swelling, or loss of function.

B. Methods of Inducing Analgesia

One embodiment provides a method of inducing analgesia in a subject in need thereof by administering to the subject a pharmaceutical composition including one or more of the disclosed ibuprofen hybrid compounds in an amount effective to reduce pain in the subject.

In one embodiment, the disclosed ibuprofen hybrid conjugates are used to relieve pain that arises from a wide range of conditions, such as but not limited to appendicitis, arthritis, bone fracture or break, burns, cancer, central pain, congenital conditions such as curvature of the spine, chronic or acute pain, cluster headaches, crash injury, dental pain, fibromyalgia, gallbladder disease, gastrointestinal disorders, headaches, herpes neuralgia, improper lifting techniques, infection, inflammatory disease, joint damage, lower back pain, menstruation, migraines, multiple sclerosis, nerve damage, neuropathic pain, a non-inflammatory neuropathic or dysfunctional pain condition, nociceptive pain, opioid resistant pain, osteoarthritis, pain during labor and delivery, pain syndromes, phantom limb pain, poor posture, post-operative pain, rheumatoid arthritis, sprains, spinal cord injury, strains, surgery, trauma, toothache, visceral pain, wound cleansing and debridement.

Pain is reported and rated by the subject experiencing it. As such, in some embodiments, the disclosed ibuprofen hybrid conjugates can reduce the level of pain reported by the subject. In some embodiments, pain is rated by the subject on a scale of 1 to 10, with 1 being no pain and 10 being extreme pain. The disclosed ibuprofen hybrid conjugates can reduce the pain by 1, 2, 3, 4, 5, 6, 7, 8, or 9 points. In some embodiments, the ibuprofen hybrid conjugates reduce pain in the subject in as little as one hour. The ibuprofen hybrid conjugates can reduce pain in as little as 1 hour, 2 hours, 3 hours, 4 hours, 5 hours, 6 hours, 8 hours, 10 hours, 12 hours, or 24 hours. In another embodiment, the ibuprofen hybrid conjugates can maintain a reduction in pain for 1 hour, 2 hours, 3 hours, 4 hours, 5 hours, 6 hours, 8 hours, 10 hours, 12 hours, 24 hours, or more than 24 hours.

In one embodiment, the subject is administered one or more of the disclosed ibuprofen conjugates every 4 hours to maintain pain relief. In another embodiment, the subject is administered one or more of the disclosed ibuprofen conjugates every 6 hours, 8 hours, 12 hours, or 24 hours to maintain pain relief.

C. Methods of Reducing Fever

One embodiment provides a method of reducing fever in a subject in need thereof by administering to the subject a pharmaceutical composition including one or more of the disclosed ibuprofen hybrid conjugates in an amount effective to reduce the fever.

Fever refers to a body temperature set-point that is elevated above the normal range of 97.7-99.5° F. (36.5-37.5° C.). Normal body temperature varies from person to person. As is well understood in the medical arts, normal body temperature typically varies with activity level and time of day, with highest temperatures observed in the afternoon and early evening hours, and lowest temperatures observed during the second half of the sleep cycle, and temperature measurements may be influenced by external factors such as mouth breathing, consumption of food or beverage, smoking, or ambient temperature (depending on the type of measurement). The normal temperature set point for individuals may vary by up to about 0.5 degrees Celsius, thus a medical professional may interpret an individual's temperature in view of these factors to diagnose whether a fever is present. Generally speaking, a fever is typically diagnosed by a core body temperature above 38.0 degrees Celsius, an oral temperature above 37.5 degrees Celsius, or an axillary temperature above 37.2 degrees Celsius.

Fever is often associated with a subjective feeling of hypothermia exhibited as a cold sensation, shivering, increased heart rate and respiration rate by which the individual's body reaches the increased set-point. Fever is usually a sign that the body is trying to fight an illness or infection. Infections cause most fevers.

In one embodiment, the disclosed ibuprofen hybrid conjugates are used to reduce fever, including, but not limited to, fever due to infections, drug reactions, allergic reactions, transfusion reactions, stroke, surgery, heat stroke, rheumatic diseases, cancer, or fever of unknown origin.

In some embodiments, the disclosed ibuprofen hybrid conjugates reduce fever in an affected individual by 0.5 to 4° C. The conjugates can reduce fever by 0.5, 0.75, 1, 1.25, 1.5, 1.75, 2, 2.25, 2.5, 2.75, 3, 3.25, 3.5, 3.75, or 4° C.

In one embodiment, administration of the disclosed ibuprofen hybrid conjugates returns the subject's body temperature to a normal range within 6-24 hours. The conjugates can return the body temperature to a normal range in 6, 7, 8, 9, 10, 11, 12, 13, 14, 15, 16, 17, 18, 19, 20, 21, 22, 23, or 24 hours.

In one embodiment, the subject is administered one or more of the disclosed ibuprofen conjugates every 4 hours to maintain fever reduction. In another embodiment, the subject is administered one or more of the disclosed ibuprofen conjugates every 6 hours, 8 hours, 12 hours, or 24 hours to maintain fever reduction.

IV. Combination Therapies

In some embodiments, the disclosed conjugate(s) is administered in combination with one or more additional active agents. The combination therapies can include administration of the active agents together in the same admixture, or in separate admixtures. Therefore, in some embodiments, the pharmaceutical composition includes two, three, or more active agents. Such formulations typically include an effective amount of one or more ibuprofen hybrid conjugate. The different active agents can have the same or different mechanisms of action. In some embodiments, the combination results in an additive effect on the treatment of the disease or disorder. In some embodiments, the combinations results in a more than additive effect on the treatment of the disease or disorder. The additional active ingredients can be chemotherapeutic agents, immunomodulatory agents, and anti-inflammatory agents. For example, the disclosed compositions can be administered to a subject in need thereof in combination with: an antimicrobial such as an antibiotic, or an antifungal, or an antiviral, or an antiparasitic, or an essential oil, or a combination thereof.

Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

The anti-inflammatory agent can be non-steroidal, steroidal, or a combination thereof. One embodiment provides oral compositions containing about 1% (w/w) to about 5% (w/w), typically about 2.5% (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

The pharmaceutical compositions can be formulated as a pharmaceutical dosage unit, also referred to as a unit dosage form.

In particular embodiments, a combination therapy includes ibuprofen hybrid conjugate(s) and one or more conventional treatments for the disease or disorder to be treated, such as those discussed herein.

EXAMPLES

Example 1. Synthesis and Chemical Analysis of Hybrid Conjugates

Materials and Methods:

Chemistry: Melting points were determined on a capillary tube melting point apparatus equipped with a digital thermometer. NMR spectra were recorded in $CDCl_3$ or DMSO-$d_6$ on a Bruker NMR spectrometer operating at 500 MHz for $^1H$ (with TMS as an internal standard) and 125 MHz for $^{13}C$. HPLC-HRMS analyses were performed on reverse phase gradient using Agilent (Santa Clara, CA) 1200 series binary pump (G1312B), waters XTerra MS C18 (3.5 um; 2.1×150 mm)+Phenomenex C18 security guard column (2×4 mm) using 0.2% acetic acid in $H_2O$/methanol as mobile phases; wavelength=254 nm; and mass spectrometry was done with 6220 Agilent (Santa Clara, CA) TOF in electrospray ionization (ESI) mode with a positive and negative method in both Profile and Centroid mode. HPLC studies were done with 6120 Agilent (quadrupole LC/MS).

Preparation of ibuprofen-amino acid conjugates: Following previously reported methods (Tiwari, A. D., et al., *Org Biomol Chem*, 7238-7249 (2014)), the benzotriazolide of ibuprofen 3 was treated with amino acids 4a-j in the presence of trimethylamine (1.5 equiv.) in acetonitrile-water (7:3) mixture at room temperature for 3 h. Each reaction mixture was poured on to ice-cold water, extracted with ethyl acetate then washed the organic layer with 4N—HCl solution (3×20 mL) followed by brine and water. Dried the ethyl acetate over anhydrous NaSO₄ and then evaporate to yield the conjugates 5a-j.

Preparation of ibuprofen hybrid conjugates with 4-aminophenol (7a j): Ibuprofen-amino acid conjugates 5a-j (1.0 equiv.) were treated with 4-aminophenol 6 (1.2 equiv.) in dimethylformamide (DMF) in the presence of N-methylmorpholinr (NMM) (1.5 equiv.) and isobutyl chloroformate (IBCF) (1.5 equiv.) at −5 to 20° C. for 6 h. Each reaction mixture was poured onto ice-cold water and the precipitate obtained was filtered, washed with water and diethyl ether to give the desired products in pure form.

Results:

Ten hybrid conjugates were synthesized through a 3-step process, outlined in Scheme 1. First, the carboxylic group of ibuprofen 1 was activated using previously reported procedures (Tiwari, A. D., et al., *Org Biomol Chem*, 7238-7249 (2014)). The benzotriazolide of ibuprofen 3 conjugated with amino acids 4a-j in the presence of triethylamine in the mixture of acetonitrile-water to yield the corresponding ibuprofen-amino acid conjugates 5a-j. Conjugates 5a-j further coupled with 4-aminophenol 6 in the presence of N-methylmorpholine (NMM) and isobutyl chloroformate (IBCF) in DMF at −5 to 20° C. for 6 h to obtain the targeted hybrid conjugates 7a-j in good yields (Scheme 1). All the synthesized compounds were fully characterized by spectral studies which are detailed below.

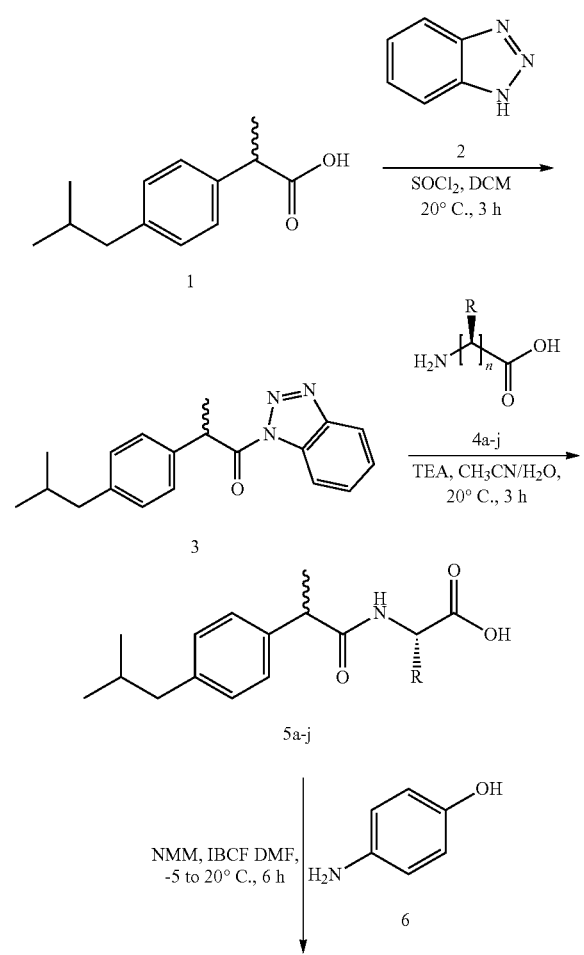

Scheme 1. Synthesis of hybrid conjugates 7a-j.

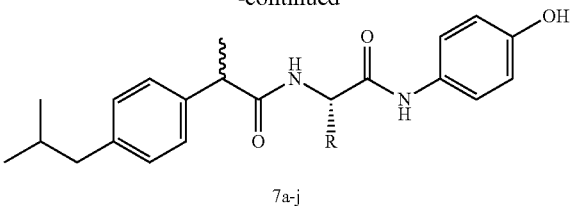

7a-j (2-(4-Isobutylphenyl)propanoyl)glycine (Ibu-Gly-OH, 5a): Colorless Oil, mp R.T., yield 90% (0.105 g). IR: $v_{max}/cm^{-1}$ 3297, 2953, 1755, 1610, 1556, 1392, 1073, 1020, 866, 848. $^1$H NMR (CDCl₃) δ: 9.77 (s, 1H), 7.10 (d, J=7.8 Hz, 2H), 7.00 (d, J=7.8 Hz, 2H), 6.51 (t, J=3.4 Hz, 1H), 4.02 (q, J=7.1, 7.15 Hz, 1H), 3.89 (dd, J=5.2, 13.3 Hz, 1H), 3.78 (dd, J=4.9, 13.6 Hz, 1H), 3.55 (q, J=67.0, 7.2 Hz, 1H), 2.33 (d, J=7.2 Hz, 2H), 1.94 (s, 1H), 1.73 (h, J=6.5, 6.6, 6.7 Hz, 1H), (d, J=7.3 Hz, 3H), 1.16 (t, J=7.1 Hz, 1H), 0.79 (d, J=6.4 Hz, 2H). $^{13}$C NMR (CDCl₃) δ: 175.8, 172.7, 171.5, 140.9, 137.5, 129.6, 127.3, 60.5, 46.2, 44.9, 41.3, 30.1, 22.3, 21.0, 18.2, 14.1.

(2-(4-Isobutylphenyl)propanoyl)-L-alanine (Ibu-L-Ala-OH, 5b): Reported previously in Sahu et al., *Synthesis*, 2013, 45(24), 3369-3374.

3-(2-(4-Isobutylphenyl)propanamido)propanoic acid (Ibu-β-Ala-OH, 5c): Colorless Oil, mp R.T., yield 95% (0.115 g). IR: $v_{max}/cm^{-1}$ 3332, 2987, 2950, 2360, 1694, 1544, 1434, 1417, 1214, 1103, 927, 776. $^1$H NMR (CDCl₃) δ: 10.51 (s, 1H), 7.09 (d, J=7.5 Hz, 2H), 7.02 (d, J=7.6 Hz, 2H), 6.16-6.08 (m, 1H), 3.47 (q, J=6.0, 6.9 Hz, 1H), 3.37 (h, J=7.0, 7.7, 6.7 Hz, 2H), 2.44 (q, J=7.6, 2.7 Hz, 2H), 2.36 (d, J=7.1 Hz, 2H), 1.76 (h, J=6.8, 6.3, 6.5 Hz, 1H), 1.41 (d, J=7.0 Hz, 3H), 0.81 (d, J=6.5 Hz, 6H). $^{13}$C NMR (CDCl₃) δ: 176.6, 175.3, 140.7, 137.9, 129.5, 127.2, 46.5, 44.9, 34.9, 33.7, 22.3, 18.3.

4-(2-(4-Isobutylphenyl)propanamido)butanoic acid (Ibu-GABA-OH, 5d): White Solid, mp 78.3° C., yield 91% (0.095 g). IR: $v_{max}/cm^{-1}$ 3290, 2951, 2867, 1698, 1645, 1550, 1427, 1314, 1256, 1204, 909, 780. $^1$H NMR (CDCl₃) δ: 11.07 (s, 1H), 7.10 (d, J=7.4 Hz, 2H), 7.00 (d, J=7.2 Hz, 2H), 6.13 (s, 1H), 4.02 (q, J=6.9, 7.1 Hz, 1H), 3.49 (q, J=7.9, 6.8 Hz, 1H), 3.15 (d, J=3.1 Hz, 2H), 2.35 (d, J=6.7 Hz, 2H), 2.19 (t, J=6.3 Hz, 2H), 1.95 (s, 1H), 1.75 (h, J=7.0, 8.4, 6.0 Hz, 1H), 1.66 (p, J=8.7, 6.1 Hz, 2H), 1.40 (d, J=6.8 Hz, 3H), 1.16 (t, J=7.1 Hz, 1H), 0.80 (d, J=3.7 Hz, 6H). $^{13}$C NMR (CDCl₃) δ: 177.1, 175.4, 171.2, 140.5, 138.1, 129.4, 127.1, 60.3, 46.3, 44.8, 38.8, 31.2, 30.0, 24.3, 22.2, 20.8, 18.1, 14.0.

(2-(4-Isobutylphenyl)propanoyl)-L-phenylalanine (Ibu-L-Phe-OH, 5e): Reported previously in Sahu et al., *Synthesis*, 2013, 45(24), 3369-3374.

(2-(4-Isobutylphenyl)propanoyl)-L-isoleucine (Ibu-L-Ile-OH, 5f): White Solid, mp 53.6° C. yield 82% (0.113 g). IR: $v_{max}/cm^{-1}$ 3343, 2961, 2869, 1716, 1625, 1538, 1512, 1461, 1383, 1144, 1071, 1006, 849, 779. $^1$H NMR (CDCl₃) δ: 11.24 (s, 1H), 7.13 (d, J=7.8 Hz, 2H), 7.04 (d, J=6.9 Hz, 2H), 5.92 (d, J=9.3 Hz, 1H), 4.48 (n, J=2.6, 4.2, 4.7, 3.0 Hz, 1H), 3.64-3.51 (m, 1H), 2.38 (d, J=6.1 Hz, 2H), 1.80-1.74 (m, 2H), 1.45 (dd, J=7.0, 10.6 Hz, 3H), 1.30-1.15 (m, 1H), 0.94-0.82 (m, 1H), 0.80 (d, J=6.7 Hz, 6H), 0.77-0.74 (m, 3H), 0.70 (dd, J=7.1, 10.4 Hz, 3H). $^{13}$C NMR (CDCl₃) δ: 180.4, 175.7, 175.6, 175.3, 174.9, 140.9, 140.8, 138.1, 137.4, 129.6, 129.3, 127.3, 127.2, 125.8, 60.5, 56.4, 56.3, 46.5, 46.4, 45.0, 44.9, 37.5, 37.4, 30.1, 24.8, 24.6, 22.3, 22.2, 18.1, 17.9, 17.8, 15.3, 15.2, 11.4.

(2-(4-Isobutylphenyl)propanoyl)-L-phenylalanine (Ibu-L-Phe-OH, 5 g) Reported previously in Sahu et al., *Synthesis*, 2013, 45(24), 3369-3374.

(2-(4-Isobutylphenyl)propanoyl)-L-isoleucine (Ibu-L-Ile-OH, 5 h): Reported previously in Sahu, et al., *Synthesis*, 45(24):3326 (2013). (2-(4-Isobutylphenyl)propanoyl)-L-methionine (Ibu-L-Met-OH, 5i): Yellowish Oil, mp R.T., yield 87% (0.0732 g). IR: $v_{max}$/cm$^{-1}$ 3303, 2953, 2916, 2868, 1722, 1446, 1366, 1274, 1218, 1120, 1073, 1002, 848, 799, 780. $^1$H NMR (CDCl$_3$) δ: 7.19 (d, J=7.8 Hz, 2H), 7.08 (d, J=7.6 Hz, 2H), 6.81 (s, 1H), 4.69-4.62 (m, 1H), 4.16-4.07 (m, 1H), 3.70-3.63 (m, 1H), 2.42 (s, 3H), 2.29 (t, J=7.2 Hz, 1H), 2.15-2.08 (m, 1H), 2.05 (s, 1H), 2.02 (s, 1H), 1.98 (s, 1H), 1.95 (s, 1H), 1.80 (p, J=5.7, 6.1 Hz, 1H), 1.48 (dd, J=7.2, 11.8 Hz, 3H), 1.23 (t, J=7.0 Hz, 1H), 0.86 (d, J=6.4 Hz, 6H). $^{13}$C NMR (CDCl$_3$) δ: 180.2, 175.5, 175.1, 171.5, 140.9, 140.8, 138.0, 137.4, 129.6, 129.3, 127.3, 127.2, 60.5, 51.5, 51.6, 46.4, 44.9, 30.9, 30.8, 30.1, 29.8, 29.6, 22.3, 21.0, 18.1, 18.0, 15.3, 15.2, 14.1.

(2-(4-Isobutylphenyl)propanoyl)-L-glutamine (Ibu-L-Gln-OH, 5j): White Solid, mp 67.4° C., yield 63% (0.073 g). IR: $v_{max}$/cm$^{-1}$ 3306, 2953, 2867, 1721, 1633, 1609, 1533, 1393, 1189, 1072, 1020, 848, 779. $^1$H NMR (CDCl$_3$) δ: 9.07 (s, 1H), 7.21 (p, J=6.9, 5.6 Hz, 2H), 7.09 (t, J=6.6 Hz, 2H), 6.77 (t, J=7.5 Hz, 1H), 6.29 (s, 1H), 4.46 (h, J=7.4, 4.8, 6.0 Hz, 1H), 3.69-3.58 (m, 1H), 2.44 (d, J=6.8 Hz, 2H), 2.33 (p, J=6.7, 6.1 Hz, 1H), 2.21-2.11 (m, 1H), 1.84 (h, J=6.0, 6.4, 6.5 Hz, 1H), 1.48 (d, J=6.6 Hz, 1H), 0.89 (d, J=5.6 Hz, 6H). $^{13}$C NMR (CDCl$_3$) δ: 177.1, 176.0, 175.8, 175.1, 175.0, 173.5, 173.3, 140.5, 140.2, 138.3, 138.0, 137.8, 129.4, 129.1, 127.1, 51.8, 51.7, 46.3, 46.2, 44.9, 44.8, 40.1, 39.9, 39.7, 39.6, 39.4, 31.6, 31.4, 30.0, 28.3, 28.1, 22.3, 22.2, 18.4, 18.3, 18.2.

N-(2-((4-Hydroxyphenyl)amino)-2-oxoethyl)-2-(4-isobutylphenyl)propanamide (Ibu-Gly-4AP, 7a): White Powder, mp 175.9° C., yield 84% (0.431 g). IR: $v_{max}$/cm$^{-1}$ 3391, 3280, 2955, 1601, 1535, 1508, 1442, 1426, 1369, 1263, 1216, 1107, 1074, 1019, 844, 810, 786. $^1$H NMR (DMSO-d$_6$) δ: 9.63 (s, 1H), 9.18 (s, 1H), 8.22 (s, 1H), 7.32 (d, J=7.7 Hz, 2H), 7.24 (d, J=7.2 Hz, 2H), 7.07 (d, J=7.4 Hz, 2H), 6.68 (d, J=7.6 Hz, 2H), 3.86 (dd, J=4.9, 11.6 Hz, 1H), 3.76 (dd, J=4.5, 11.8 Hz, 1H), 3.70 (q, J=6.7, 6.9 Hz, 1H), 2.40 (d, J=6.9 Hz, 2H), 1.80 (h, J=6.5, 6.6, 6.6 Hz, 1H), 1.33 (d, J=6.7 Hz, 3H), 0.85 (d, J=6.4 Hz, 6H). $^{13}$C NMR (DMSO-d$_6$) δ: 173.9, 166.9, 153.3, 139.4, 139.2, 130.5, 128.7, 127.1, 120.8, 115.1, 44.4, 44.2, 42.6, 29.6, 22.2, 18.6. HRMS m/z for C$_{21}$H$_{26}$N$_2$O$_3$ [M+H]$^+$ Calcd. 355.2016. Found: 355.2011.

(2S)-N-(4-Hydroxyphenyl)-2-(2-(4-isobutylphenyl)propanamido)propanamide (Ibu-L-Ala-4AP, 7b): Brown Powder, mp 193.7° C., yield 45% (0.157 g). IR: $v_{max}$/cm$^{-1}$ 3156, 2960, 1635, 1559, 1248, 1229, 831, 744. $^1$H NMR (DMSO-d$_6$) δ: 9.72 (s, 1H), 8.17 (d, J=7.3 Hz, 1H), 7.37 (d, J=8.8 Hz, 2H), 7.23 (d, J=8.0 Hz, 2H), 7.07 (d, J=8.0 Hz, 2H), 6.69 (d, J=8.8 Hz, 2H), 4.32 (p, J=7.1, 7.2 Hz, 1H), 3.69 (q, J 7.1, 7.0 Hz, 1H), 2.40 (d, J=7.1 Hz, 2H), 1.80 (h, J=6.6, 6.8, 6.7 Hz, 1H), 1.29 (d, J=7.1 Hz, 3H), 1.20 (d, J=7.1 Hz, 3H), 0.85 (d, J=6.6 Hz, 6H). $^{13}$C NMR (DMSO-d$_6$) δ: 173.3, 170.6, 153.3, 139.5, 139.2, 130.7, 128.7, 120.8, 115.0, 48.9, 44.3, 44.1, 29.6, 22.2, 18.5, 18.2. HRMS m/z for C$_{22}$H$_{28}$N$_2$O$_3$ [M+H]$^+$ Calcd. 369.2173. Found: 369.2172.

N-(4-Hydroxyphenyl)-3-(2-(4-isobutylphenyl)propanamido)propanamide (Ibu-β-Ala-4AP, 7c): White Powder, mp 155.5° C., yield 93% (0.663 g). IR: $v_{max}$/cm$^{-1}$ 3295, 2952, 1608, 1510, 1454, 1364, 1225, 1078, 830. $^1$H NMR (DMSO-d$_6$) δ: 9.63 (s, 1H), 8.02 (s, 1H), 7.34 (d, J=7.9 Hz, 2H), 7.18 (d, J=7.5 Hz, 2H), 7.02 (d, J=7.45 Hz, 2H), 6.66 (d, J=7.9 Hz, 2H), 3.55 (q, J=6.2 Hz, 6.9 Hz, 1H), 3.28 (d, J=5.1 Hz, 2H), 2.40-2.36 (m, 4H), 1.77 (h, J=6.35, 6.6, 6.6 Hz, 1H), 1.28 (d, J=6.8 Hz, 3H), 0.83 (d, J=6.4 Hz, 6H). $^{13}$C NMR (DMSO-d$_6$) δ: 173.5, 168.6, 153.1, 139.5, 139.1, 130.9, 128.7, 126.9, 120.8, 114.9, 44.5, 44.2, 36.1, 35.3, 29.6, 22.2, 18.5. HRMS m/z for C$_{22}$H$_{28}$N$_2$O$_3$ [M+H]$^+$ Calcd. 369.2173. Found: 369.2174.

N-(4-Hydroxyphenyl)-4-(2-(4-isobutylphenyl)propanamido)butanamide (Ibu-GABA-4AP, 7d): White Powder, mp 140.6° C., yield 83% (0.376 g). IR: $v_{max}$/cm$^{-1}$ 3308, 2953, 1610, 1539, 1444, 1368, 1234, 829. $^1$H NMR (DMSO-d$_6$) δ: 9.59 (s, 1H), 9.12 (s, 1H), 7.95 (s, 1H), 7.33 (d, =8.0 Hz, 2H), 7.20 (d, J=7.3 Hz, 2H), 7.06 (d, J=7.3 Hz, 2H), 6.66 (d, J=8.0 Hz, 2H), 3.52 (q, J=6.6, 7.4 Hz, 1H), 3.04 (dp, J=4.2, 7.3, 7.1, 6.5, 8.1 Hz, 2H), 2.39 (d, J=6.7 Hz, 2H), 2.20 (t, J=6.6 Hz, 2H), 1.78 (h, J=7.1, 6.9, 6.9 Hz, 1H), 1.66 (t, J=6.6 Hz, 2H), 1.30 (d, J=6.4 Hz, 3H), 0.84 (d, J=6.1 Hz, 6H). $^{13}$C NMR (DMSO-d$_6$) δ: 173.4, 170.0, 153.1, 139.6, 139.1, 131.0, 128.7, 126.9, 120.8, 114.9, 44.8, 44.2, 38.3, 33.6, 29.6, 25.7, 22.2, 18.6. HRMS m/z for C$_{23}$H$_{30}$N$_2$O$_3$ [M+H]$^+$ Calcd. 382.2256. Found: 382.2256.

(2S)-N-(4-Hydroxyphenyl)-2-(2-(4-isobutylphenyl)propanamido)-3-phenylpropanamide (Ibu-L-Phe-4AP, 7e): White Powder, mp 168.7° C., yield 38% (0.112 g). IR: $v_{max}$/cm$^{-1}$ 3387, 3277, 2955, 1644, 1543, 1507, 1434, 1367, 1268, 1212, 1179, 833, 732. $^1$H NMR (DMSO-d$_6$) δ: 9.80 (s, 1H), 9.20 (d, J=9.3 Hz, 1H), 8.25 (dd, J=7.9, 22.7 Hz, 1H), 7.36 (d, J=7.6 Hz, 1H), 7.28, (s, 3H), 7.19, (s, 1H), 7.17 (d, J=7.55 Hz, 1H), 7.11 (s, 2H), 7.09 (d, J=9.0 Hz, 1H), 7.01 (t, J=10.6 Hz, 2H), 6.71 (d, J=7.75 Hz, 1H), 6.67 (d, J=7.7 Hz, 1H), 4.63 (dq, J=8.0, 4.6, 8.3, 16.3 Hz, 1H), 3.67 (h, J=6.4, 6.8, 6.7 Hz, 1H), 3.04-2.80 (m, 2H), 2.38 (t, J=8.6 Hz, 2H), 1.79 (n, J=5.6, 6.5, 6.45, 6.6 Hz, 1H), 1.21 (dd, J=6.4, 51.5 Hz, 3H), 0.84 (q, J=6.3, 6.8 Hz, 6H). $^{13}$C NMR (DMSO-d$_6$) δ: 173.3, 169.4, 169.2, 153.4, 139.2, 139.1, 139.0, 137.7, 137.5, 130.4, 130.3, 129.3, 129.1, 128.7, 128.6, 128.0, 127.9, 127.0, 126.9, 126.3, 126.1, 121.1, 115.1, 115.0, 139.2, 139.1, 139.0, 137.7, 137.5, 130.4, 130.3, 129.3, 129.1, 128.7, 128.6, 128.0, 127.9, 127.0, 126.9, 126.3, 126.1, 54.5, 54.4, 44.3, 44.2, 44.1, 38.2, 37.8, 29.7, 29.6, 22.2, 18.7, 17.9. HRMS m/z for C$_{28}$H$_{32}$N$_2$O$_3$ [M+H]$^+$ Calcd. 445.2486. Found: 445.2489.

(2S,3S)-N-(4-Hydroxyphenyl)-2-(2-(4-isobutylphenyl)propanamido-3-methylpentanamide (Ibu-L-Ile-4AP, 7f): Off-White Powder, mp 205° C., yield 67% (0.096 g). IR: $v_{max}$/cm$^{-1}$ 3389, 3273, 2966, 1600, 15099, 1438, 1381, 1368, 1268, 1218, 1105, 786, 756. $^1$H NMR (DMSO-d$_6$) δ: 9.72 (s, 1H), 9.16 (s, 1H), 8.05 (dd, J=8.6, 29.9 Hz, 1H), 7.29 (d, J=7.0 Hz, 2H), 7.21 (d, J=7.3 Hz, 2H), 7.04 (d, J=5.8 Hz, 2H), 6.65 (d, J=8.0 Hz, 2H), 4.35 (dt, J=6.9, 7.9, 48 Hz, 1H), 3.84-3.78 (m, 1H), 2.37 (d, J=6.35 Hz, 2H), 1.78 (h, J=9.7, 6.9, 5.0 Hz, 2H), 1.49 (h, J=6.8, 7.5, 4.2 Hz, 1H), 1.31 (d, J=5.1 Hz, 3H), 1.13 (h, J=7.2, 7.6, 6.2 Hz, 1H), 0.89-0.82 (m, 12H). $^{13}$C NMR (DMSO-d$_6$) δ: 173.5, 169.4, 153.4, 139.3, 139.1, 130.3, 128.7, 127.1, 121.0, 115.0, 57.2, 56.5, 44.2, 44.1, 37.4, 36.9, 29.6, 25.8, 24.5, 22.2, 18.9, 15.3, 14.7, 11.5, 10.9. HRMS m/z for C$_{25}$H$_{34}$N$_2$O$_3$ [M+H]$^+$ Calcd. 410.2569.

(2S)-N-(4-Hydroxyphenyl)-2-(2-(4-isobutylphenyl)propanamido)-4-methylpentanamide (Ibu-L-Leu-4AP, 7 g): Off-White Powder, mp 230.5° C., yield 76% (0.151 g). IR:

$v_{max}$/cm$^{-1}$ 3281, 2957, 2360, 1646, 1529, 1510, 1439, 1370, 1266, 1218, 1190, 832, 807, 785. $^1$H NMR (DMSO-d$_6$) δ: 9.63 (s, 1H), 9.17 (s, 1H), 8.17 (d, J=7.7 Hz, 1H), 7.28 (d, J=8.1 Hz, 2H), 7.21 (d, J=7.4 Hz, 2H), 7.04 (d, J=7.0 Hz, 2H), 6.65 (d, J=7.8 Hz, 2H), 4.43 (q, J=8.0, 5.4 Hz, 1H), 3.71 (q, J=8.2, 6.7 Hz, 1H), 2.38 (d, J=6.8 Hz, 2H), 1.78 (h, J=7.6, 6.0, 6.25 Hz, 1H), 1.62 (p, J=7.1, 6.3 Hz, 1H), 1.57-1.45 (m, 2H), 1.31 (d, J=6.6 Hz, 3H), 0.91 (d, J=5.7 Hz, 3H), 0.88 (d, J=5.7 Hz, 3H), 0.83 (d, J=5.4 Hz, 6H). $^{13}$C NMR (DMSO-d$_6$) δ: 173.4, 170.2, 153.3, 139.3, 139.1, 130.4, 128.7, 127.0, 120.9, 115.0, 51.6, 44.2, 41.2, 29.6, 24.4, 22.9, 22.2, 21.8, 18.76. HRMS m/z for C$_{25}$H$_{34}$N$_2$O$_3$ [M+H]$^+$ Calcd. 411.2642. Found: 411.2644.

(2S)-N-(4-Hydroxyphenyl)-2-(2-(4-isobutylphenyl)propanamido)-3-methylbutanamide (Ibu-L-Val-4AP, 7 h): White Powder, mp 202.2° C., yield 35% (0.055 g). IR: $v_{max}$/cm$^{-1}$ 3389, 3270, 2962, 2870, 1601, 1530, 1510, 1439, 1370, 1270, 1218, 1106, 871, 833, 847, 813, 786. $^1$H NMR (DMSO-d$_6$) δ: 9.71 (s, 1H), 9.16 (s, 1H), 8.06 (d, J=8.6 Hz, 1H), 7.29 (d, J=7.6 Hz, 2H), 7.22 (d, J=7.1 Hz, 2H), 7.04 (d, J=7.3 Hz, 2H), 6.65 (d, J=7.5 Hz, 2H), 4.27 (t, J=7.7 Hz, 1H), 3.81 (q, J=7.0, 6.7 Hz, 1H), 2.37 (d, J=6.7 Hz, 2H), 1.99 (sex, J=8.85, 6.2, 6.3 Hz, 1H), 1.78 (h, J=7.4, 6.3, 6.35 Hz, 1H), 1.32 (d, J=6.2 Hz, 3H), 0.89 (d, J=5.9 Hz, 6H), 0.83 (d, J=6.05 Hz, 6H). $^{13}$C NMR (DMSO-d$_6$) δ: 173.6, 169.3, 153.4, 139.3, 139.1, 130.3, 128.7, 127.0, 121.0, 115.0, 58.2, 44.2, 44.0, 31.0, 29.6, 22.2, 19.2, 19.0, 18.4. HRMS m/z for C$_{24}$H$_{32}$N$_2$O$_3$ [M+H]$^+$ Calcd. 397.2486. Found: 397.2486.

(2S)-N-(4-Hydroxyphenyl)-2-(2-(4-isobutylphenyl)propanamido)-4-(methylthio)butanamide (Ibu-L-Met-4AP, 7i): White Powder, mp 190.8° C., yield 73% (0.141 g). IR: $v_{max}$/cm$^{-1}$ 3396, 3268, 1599, 1508, 1440, 1370, 1264, 1217, 1191, 841, 815, 785. $^1$H NMR (DMSO-d$_6$) δ: 9.61 (s, 1H), 9.18 (s, 1H), 8.24 (d, J=7.9 Hz, 1H), 7.26 (d, J=8.4 Hz, 2H), 7.22 (d, J=7.6 Hz, 2H), 7.05 (d, J=7.7 Hz, 2H), 6.65 (d, J=8.3 Hz, 2H), 4.45 (q, J=7.4, 6.1 Hz, 1H), 3.72 (q, J=6.5, 6.9 Hz, 1H), 2.38 (d, J=7.0 Hz, 2H), 2.05 (s, 3H), 1.95 (sex, J=5.5, 7.8, 6.6 Hz, 1H), 1.89-1.85 (m, 1H), 1.78 (h, J=7.4, 6.6, 6.6 Hz, 1H), 1.32 (d, J=7.0 Hz, 3H), 0.83 (d, J=6.4 Hz, 6H). $^{13}$C NMR (DMSO-d$_6$) δ: 173.6, 169.2, 153.4, 139.2, 130.3, 128.7, 127.0, 121.0, 115.0, 99.5, 52.4, 44.2, 32.1, 29.6, 22.2, 18.8, 18.0, 14.7, 14.6. HRMS m/z for C$_{25}$H$_{34}$N$_2$O$_3$S [M+H]$^+$ Calcd. 429.2134. Found: 429.2206.

(2S)—N1-(4-Hydroxyphenyl)-2-(2-(4-isobutylphenyl)propanamido)pentanediamide (Ibu-L-Gln-4AP, 7j): Yellowish Powder, mp 148.3° C., yield 41% (0.046 g). IR: $v_{max}$/cm$^{-1}$ 3288, 2953, 1538, 1447, 1365, 1293, 1224, 1166, 831. $^1$H NMR (DMSO-d$_6$) δ: 9.77 (s, 1H), 9.60 (s, 1H), 9.19 (d, J=8.2, 1H), 8.19 (t, J=7.5, 1H), 7.37 (d, J=8.5, 1H), 7.27 (d, J=8.2, 1H), 7.23 (t, 8.5, 2H), 7.04 (t, J=11.2, 2H), 6.78 (s, 1H), 6.69 (d, J=8.4, 1H), 6.65 (d, J=8.35, 1H), 4.31 (dq, J=7.0, 6.9, 6.7, 22.6, 1H), 3.72 (q, J=5.9, 7.0, 1H), 2.39 (t, J=7.85). $^{13}$C NMR (DMSO-d$_6$) δ: 173.4, 170.0, 153.1, 139.6, 139.1, 131.0, 128.7, 126.9, 120.8, 114.9, 44.8, 44.2, 38.3, 33.6, 29.6, 25.7, 22.2, 18.6. HRMS m/z for C$_{23}$H$_{30}$N$_2$O$_3$ [M+H]$^+$ Calcd. 382.2256. Found: 382.2256.

Example 2: Biological Studies—Anti-Inflammation Properties

Figure 3:
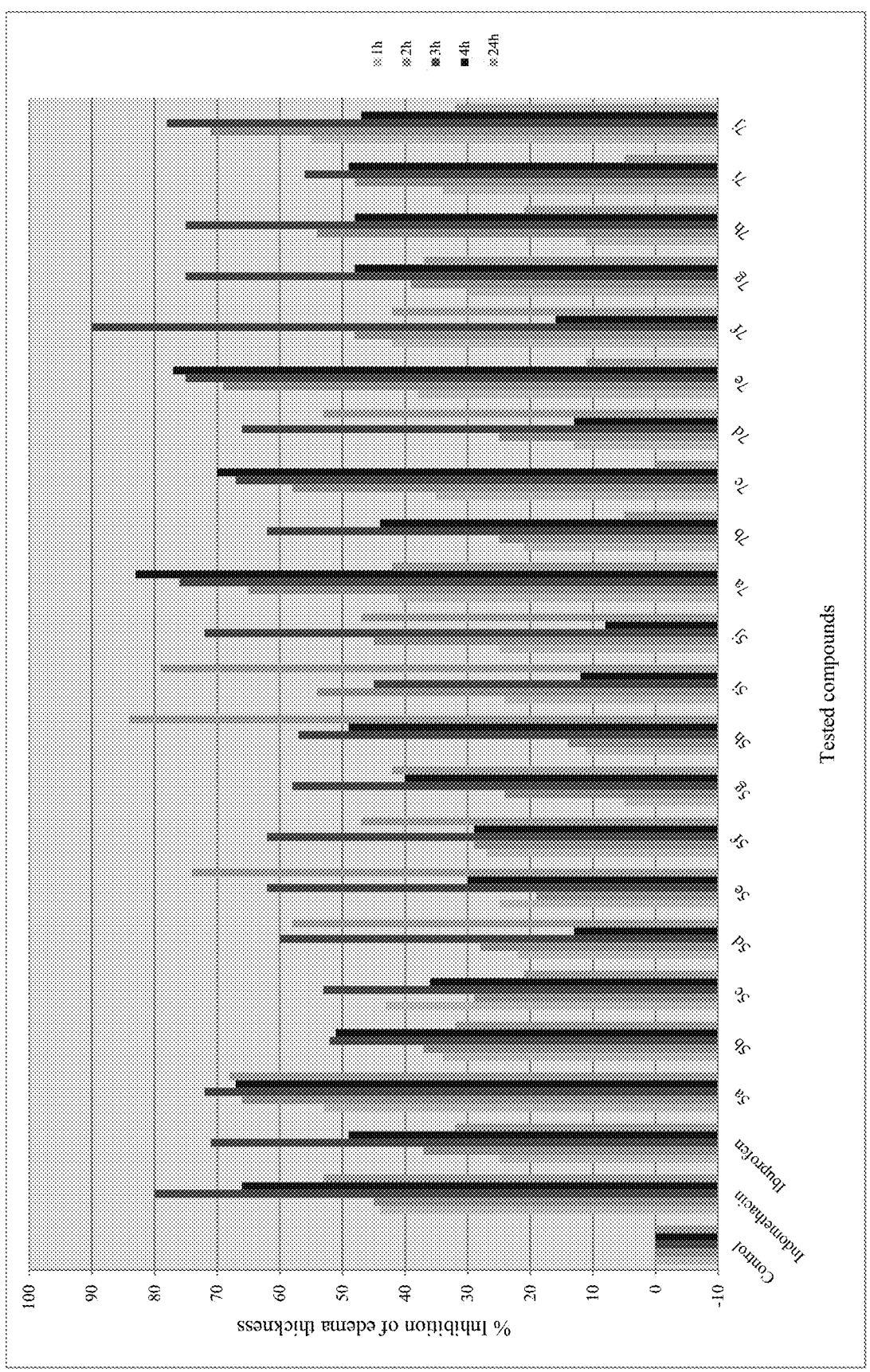
FIG. 3 is a bar graph showing percent inhibition of edema thickness for the compounds at successive time intervals from left to right (1 hour, 2 hour, 3 hour, 4 hour, and 24 hour).

Materials and Methods:

Anti-inflammatory properties of the ibuprofen-amino acid conjugate (5a-j) and ibuprofen-amino acid-4-aminophenol conjugates 7a-j were studied by the standard carrageenan-induced paw edema technique (Naumov, R. N. et al., *Bioorg. Med. Chem. Lett.* 2015, 25, 2314-2320; Tiwari, A. D. et al., *Org. Biomol. Chem.* 2014, 12, 7238-7249). The observed properties were compared with the clinically used NSAIDs (standard references) indomethacin and ibuprofen (Table 1, FIG. 3).

Results:

Some of the constructed conjugates revealed enhanced biological properties with potency higher than the used standards. Compound 7f (Ibu-L-Ile-4AP) was superior among all the tested compounds (potency "% inhibition relative to indomethacin"=113). Few synthesized conjugates [5a (Ibu-Gly-OH), 5j (Ibu-L-Gln-OH), 7a (Ibu-Gly-4AP), 7e (Ibu-L-Phe-4AP), 7 g (Ibu-L-Leu-4AP), 7 h (Ibu-L-Val-4AP), 7j (Ibu-L-Gln-4AP)] also showed higher potency than ibuprofen (potency=98-90 compared with ibuprofen of potency=89). Based on the observed biological properties few SAR (structure-activity relationships) could be obtained. The ibuprofen-amino acid-4-aminophenol conjugates 7a-j were of higher anti-inflammatory power than their corresponding ibuprofen-amino acids 5a-j, explaining the effect of 4-aminophenol residue in enhancing the biological properties. However, the ibuprofen-amino acid conjugates revealed prolonged biological activity compared to their analogs of aminophenol residue considering the properties revealed at the 24 h effect. This explains their accessibility for chronic use. α-Amino acid seems more appropriate than theft-analogs for developing promising anti-inflammatory active conjugates as exhibited by the synthesized agents with glycine (5a and 7a) and β-alanine (5c and 7c). Additionally, branching of the α-amino amino acid is a controlling factor governing the anti-inflammatory activity revealed (as exhibited in compounds 5f/5g/5h and 7f/7g/7h).

TABLE 1

Anti-inflammatory results of the tested compounds.

| Entry | Compd. | Mean edema thickness "mm" (% inhibition of edema) | | | | | Potency[a] |
|---|---|---|---|---|---|---|---|
| | | 1 h | 2 h | 3 h | 4 h | 24 h | |
| 1 | Control | 1.23 ± 0.03 | 1.51 ± 0.04 | 1.30 ± 0.02 | 1.25 ± 0.01 | 0.19 ± 0.02 | — |

TABLE 1-continued

Anti-inflammatory results of the tested compounds.

| Entry | Compd. | Mean edema thickness "mm" (% inhibition of edema) | | | | | Potency[a] |
|---|---|---|---|---|---|---|---|
| | | 1 h | 2 h | 3 h | 4 h | 24 h | |
| 2 | Indomethacin | 0.69 ± 0.05 (44) | 0.83 ± 0.04 (45) | 0.26 ± 0.03 (80) | 0.43 ± 0.05 (66) | 0.09 ± 0.02 (53) | 100 |
| 3 | 1 Ibuprofen | 0.92 ± 0.02 (25) | 0.95 ± 0.03 (37) | 0.38 ± 0.01 (71) | 0.64 ± 0.02 (49) | 0.13 ± 0.01 (32) | 89 |
| 4 | 5a (Ibu-Gly-OH) | 0.58 ± 0.02 (53) | 0.51 ± 0.04 (66) | 0.37 ± 0.06 (72) | 0.41 ± 0.04 (67) | 0.06 ± 0.01 (68) | 90 |
| 5 | 5b (Ibu-L-Ala-OH) | 0.81 ± 0.04 (34) | 0.95 ± 0.02 (37) | 0.63 ± 0.01 (52) | 0.61 ± 0.03 (51) | 0.13 ± 0.03 (32) | 65 |
| 6 | 5c (Ibu-β-Ala-OH) | 0.70 ± 0.03 (43) | 1.07 ± 0.07 (29) | 0.61 ± 0.04 (53) | 0.80 ± 0.03 (36) | 0.15 ± 0.01 (21) | 66 |
| 7 | 5d (Ibu-GABA-OH) | 0.96 ± 0.06 (22) | 1.09 ± 0.07 (28) | 0.52 ± 0.04 (60) | 1.09 ± 0.05 (13) | 0.08 ± 0.02 (58) | 75 |

TABLE 1-continued

Anti-inflammatory results of the tested compounds.

| Entry | Compd. | Mean edema thickness "mm" (% inhibition of edema) | | | | | Potency[a] |
|---|---|---|---|---|---|---|---|
| | | 1 h | 2 h | 3 h | 4 h | 24 h | |
| 8 | 5e (Ibu-L-Phe-OH) | 0.92 ± 0.07 (25) | 1.22 ± 0.08 (19) | 0.50 ± 0.04 (62) | 0.88 ± 0.05 (30) | 0.05 ± 0.02 (74) | 78 |
| 9 | 5f (Ibu-L-Ile-OH) | 0.90 ± 0.05 (27) | 1.07 ± 0.06 (29) | 0.50 ± 0.03 (62) | 0.89 ± 0.04 (29) | 0.10 ± 0.03 (47) | 78 |
| 10 | 5g (Ibu-L-Leu-OH) | 1.17 ± 0.07 (5) | 1.15 ± 0.06 (24) | 0.55 ± 0.04 (58) | 0.75 ± 0.05 (40) | 0.11 ± 0.04 (42) | 73 |
| 11 | 5h (Ibu-L-Val-OH) | 1.09 ± 0.08 (11) | 1.30 ± 0.07 (14) | 0.56 ± 0.05 (57) | 0.64 ± 0.06 (49) | 0.03 ± 0.02 (84) | 72 |
| 12 | 5i (Ibu-L-Met-OH) | 0.93 ± 0.04 (24) | 0.69 ± 0.05 (54) | 0.71 ± 0.04 (45) | 1.10 ± 0.06 (12) | 0.04 ± 0.01 (79) | 56 |
| 13 | 5j (Ibu-L-Gln-OH) | 0.92 ± 0.05 (25) | 0.83 ± 0.04 (45) | 0.36 ± 0.02 (72) | 1.15 ± 0.06 (8) | 0.10 ± 0.03 (47) | 90 |

TABLE 1-continued

Anti-inflammatory results of the tested compounds.

| Entry | Compd. | Mean edema thickness "mm" (% inhibition of edema) | | | | | Potency[a] |
|---|---|---|---|---|---|---|---|
| | | 1 h | 2 h | 3 h | 4 h | 24 h | |
| 14 | 7a (Ibu-Gly-4AP) | 0.73 ± 0.04 (41) | 0.53 ± 0.03 (65) | 0.31 ± 0.02 (76) | 0.21 ± 0.02 (83) | 0.11 ± 0.03 (42) | 95 |
| 15 | 7b (Ibu-L-Ala-AP) | 0.97 ± 0.05 (21) | 1.13 ± 0.06 (25) | 0.50 ± 0.02 (62) | 0.70 ± 0.03 (44) | 0.18 ± 0.02 (5) | 78 |
| 16 | 7c (Ibu-β-Ala-4AP) | 0.80 ± 0.03 (35) | 0.63 ± 0.03 (58) | 0.43 ± 0.02 (67) | 0.38 ± 0.01 (70) | 0.19 ± 0.02 (0) | 84 |
| 17 | 7d (Ibu-GABA-4AP) | 1.07 ± 0.06 (13) | 1.14 ± 0.04 (25) | 0.44 ± 0.03 (66) | 1.09 ± 0.04 (13) | 0.09 ± 0.01 (53) | 83 |
| 18 | 7e (Ibu-L-Phe-4AP) | 0.76 ± 0.05 (38) | 0.47 ± 0.03 (69) | 0.32 ± 0.01 (75) | 0.29 ± 0.03 (77) | 0.17 ± 0.03 (11) | 94 |
| 19 | 7f (Ibu-L-Ile-4AP) | 0.71 ± 0.01 (42) | 0.79 ± 0.04 (48) | 0.13 ± 0.02 (90) | 1.05 ± 0.05 (16) | 0.11 ± 0.02 (42) | 113 |

TABLE 1-continued

Anti-inflammatory results of the tested compounds.

| Entry | Compd. | Mean edema thickness "mm" (% inhibition of edema) | | | | | Potency[a] |
|---|---|---|---|---|---|---|---|
| | | 1 h | 2 h | 3 h | 4 h | 24 h | |
| 20 | 7g (Ibu-L-Leu-4AP) | 0.86 ± 0.03 (30) | 0.92 ± 0.04 (39) | 0.33 ± 0.03 (75) | 0.65 ± 0.03 (48) | 0.12 ± 0.03 (37) | 94 |
| 21 | 7h (Ibu-L-Val-4AP) | 1.09 ± 0.06 (11) | 0.69 ± 0.05 (54) | 0.32 ± 0.03 (75) | 0.65 ± 0.04 (48) | 0.15 ± 0.03 (21) | 94 |
| 22 | 7i (Ibu-L-Met-4AP) | 0.81 ± 0.04 (34) | 0.79 ± 0.04 (48) | 0.57 ± 0.02 (56) | 0.64 ± 0.03 (49) | 0.18 ± 0.02 (5) | 70 |
| 23 | 7j (Ibu-L-Gln-4AP) | 0.55 ± 0.04 (55) | 0.44 ± 0.02 (71) | 0.28 ± 0.01 (78) | 0.66 ± 0.03 (47) | 0.13 ± 0.03 (32) | 98 |

[a] % Inhibition relative to indomethacin at 3 h effect.

Example 3: Biological Studies—Ulcerogenic Liability

Materials and Methods:

The conjugates synthesized with potent anti-inflammatory properties (5a,j, and 7a,e-h,j) relative to their precursor (ibuprofen) were subject to ulcerogenic liability utilizing the standard technique applying the same dose of anti-inflammatory testing (Naumov, R. N. et al., *Bioorg. Med. Chem. Lett.* 2015, 25, 2314-2320; Tiwari, A. D. et al., *Org. Biomol. Chem.* 2014, 12, 7238-7249).

Results:

From the results observed (Table 2) it is obvious that the synthesized compounds of the present study are of safe ulcerogenic profile (no ulcers or lesions in the animal gastric mucosa) relative to the standard references (ulcer index=13.67, 4.33 for indomethacin and ibuprofen, respectively). These observations are comparable with that of celecoxib (selective COX-2 inhibitor) (Kucukguzel, S. G. et al., *Molecules* 2013, 18, 3595-3614; Abdellatif, K. R. A. et al., *J. Enzyme Inhib. Med. Chem.* 2016, 31, 1545-1555).

Example 4: Biological Studies—Toxicological Studies

Materials and Methods:

The synthesized conjugates with potent anti-inflammatory properties (5a,j, and 7a,e-h,j) relative to their precursor (ibuprofen) were subject to toxicological studies utilizing the standard technique applying 5 and 10 folds of the anti-inflammatory dose (Naumov, R. N. et al., *Bioorg. Med. Chem. Lett.* 2015, 25, 2314-2320; Tiwari, A. D. et al., *Org. Biomol. Chem.* 2014, 12, 7238-7249).

Results:

A safe profile (no toxic symptoms) was revealed by all the tested compounds due to the applied doses.

Example 5: Biological Studies—Peripheral Analgesic Properties

Materials and Methods

Peripheral analgesic properties of the synthesized conjugates were determined by the standard in vivo acetic acid-induced abdominal writhing technique (Amin, K. M., et al., *Eur. J. Med. Chem.* 2009, 44, 4572-4584).

Results:

From the observed results (Table 3), it can be concluded that conjugates containing 4-aminophenol 7a-j afford enhanced analgesic properties compared to the corresponding analogs lack this fragment 5a-j. The α-amino acid containing conjugates are of higher analgesic properties than those of γ- and γ-amino acids (as revealed by conjugates 5a/5c/5d and 7a/7c/7d; potency=83/8/7, 139/115/77, respectively). Type of amino acid is also a controlling factor for the biological activity revealed (leucine and isoleucine seem superior among all the amino acid used).

TABLE 2

Ulcerogenic liability for the tested conjugates.

| Entry | Compd. | Number of animals with ulcer | % Incidence of ulcer divided by 10 | Average of ulcer number | Average severity of ulcer | Ulcer index |
|---|---|---|---|---|---|---|
| 1 | Control | 0/6 | 0 | 0 | 0 | 0 |
| 2 | Indomethacin | 6/6 | 10 | 2 | 1.67 | 13.67 |
| 3 | Ibuprofen | 2/6 | 3.33 | 0.33 | 0.67 | 4.33 |
| 4 | 5a | 0 | 0 | 0 | 0 | 0 |
| 5 | 5j | 0 | 0 | 0 | 0 | 0 |
| 6 | 7a | 0 | 0 | 0 | 0 | 0 |
| 7 | 7e | 0 | 0 | 0 | 0 | 0 |
| 8 | 7f | 0 | 0 | 0 | 0 | 0 |
| 9 | 7g | 0 | 0 | 0 | 0 | 0 |
| 10 | 7h | 0 | 0 | 0 | 0 | 0 |
| 11 | 7j | 0 | 0 | 0 | 0 | 0 |

Example 6: Biological Studies—Central Analgesic Properties

Materials and Methods:

Central analgesic properties of the synthesized conjugates were determined by the standard in vivo hot plate technique (Eddy, N. B., et al., *J Pharmacol. Exp. Ther.* 1953, 107, 385-393; Sarigol, D., et al., *Bioorg. Med. Chem.* 2015, 23, 2518-2528).

Results:

It has been noticed that (Table 4), the results revealed central analgesic propertied are similar to that of the peripheral analgesic observations. The conjugates bearing 4-aminophenol residue 7a-j are more effective agents than their analogs lacking this moiety 5a-j. The type of amino acid is also important in developing the total analgesic properties observed (isoleucine is superior among all the amino acid used, the potency of 7f=2.9 folds of indomethacin). Conjugates 7e, 7i and 7j also show high central analgesic properties=2.15-2.55 folds of indomethacin.

Example 7: Biological Studies—COX-1/2 Assay

Materials and Methods:

Cyclooxygenases (COX) are the key enzymes capable of the conversion of arachidonic acid to prostaglandins. This is why inhibition of COX enzymes seems a fruitful approach for inflammation inhibition (Rayar, A. M., et al., *Eur. J. Med. Chem.* 2018, 146, 577-587; Girgis, A. S., et al., *Eur. J. Med. Chem.* 2012, 50, 1-8). The potent anti-inflammatory active conjugates synthesized (7a,e-h,j) were subjected to COX-1/2 bio-assay which can indicate their mode of action.

Results:

From the results obtained (Table 5), it can be concluded that the COX-1/2 inhibitory properties of the tested compounds support the in-vivo anti-inflammatory observations (Table 1). Compound 7e reveals enhanced inhibitory properties towards COX-2 compared to its parent precursor, ibuprofen [selectivity index "$SI_{(COX-2/COX-1)}$"=5.3, 11.6 for 7e and ibuprofen, respectively]. Meanwhile, compound 7h and 7j exhibit selectivity index towards the tested cyclooxygenase enzymes relatively similar to that of ibuprofen (SI=12.8, 14.0 for 7h and 7j, respectively). Compound 7g reveals higher affinity/selectivity toward COX-1 relative to its parent precursor, ibuprofen (SI=54.3). Similar observations were also shown by compounds 7a and 7f (SI=29.0).

TABLE 3

Peripheral analgesic properties of the tested compounds.

| Entry | Compd. | Writing reflex ± SEM | % Inhibition/ protection | Potency* |
|---|---|---|---|---|
| 1 | Control | 97.3 ± 1.5 | 0 | — |
| 2 | Indomethacin | 43.9 ± 1.9 | 54.9 | 100 |
| 3 | Ibuprofen | 47.9 ± 2.1 | 50.8 | 93 |
| 4 | 5a | 52.9 ± 1.3 | 45.6 | 83 |
| 5 | 5b | 54.7 ± 2.0 | 43.8 | 80 |
| 6 | 5c | 93.2 ± 1.4 | 4.2 | 8 |
| 7 | 5d | 93.6 ± 2.6 | 3.8 | 7 |
| 8 | 5e | 52.5 ± 1.2 | 46.0 | 84 |
| 9 | 5f | 51.8 ± 1.6 | 46.8 | 85 |
| 10 | 5g | 49.7 ± 1.2 | 48.9 | 89 |
| 11 | 5h | 68.5 ± 2.0 | 29.6 | 54 |
| 12 | 5i | 75.7 ± 1.9 | 22.2 | 40 |
| 13 | 5j | 95.7 ± 2.4 | 1.6 | 3 |
| 14 | 7a | 23.0 ± 0.9 | 76.4 | 139 |
| 15 | 7b | 26.7 ± 1.1 | 72.6 | 132 |
| 16 | 7c | 36.0 ± 1.3 | 63.0 | 115 |
| 17 | 7d | 56.3 ± 0.7 | 42.1 | 77 |
| 18 | 7e | 25.7 ± 1.0 | 73.6 | 134 |
| 19 | 7f | 14.3 ± 0.8 | 85.3 | 155 |
| 20 | 7g | 20.3 ± 0.9 | 79.1 | 144 |
| 21 | 7h | 24.0 ± 0.4 | 75.3 | 137 |
| 22 | 7i | 28.8 ± 1.0 | 70.4 | 128 |
| 23 | 7j | 79.0 ± 1.8 | 18.8 | 34 |

*Relative to indomethacin.

TABLE 4

Central analgesic properties of the tested compounds.

| Entry | Compd. | After 0 min. | After 30 min. | After 60 min. |
|---|---|---|---|---|
| 1 | Control | 2.96 ± 0.05 (0) | 2.42 ± 0.04 (0) | 2.23 ± 0.05 (0) |
| 2 | Indomethacin | 3.15 ± 0.03 (6.4) | 3.16 ± 0.02 (30.6) | 3.02 ± 0.04 (35.4) |
| 3 | Ibuprofen | 3.14 ± 0.06 (6.1) | 3.03 ± 0.04 (25.2) | 2.91 ± 0.02 (30.5) |
| 4 | 5a | 3.01 ± 0.01 (1.7) | 2.79 ± 0.03 (15.3) | 2.86 ± 0.04 (28.3) |
| 5 | 5b | 3.25 ± 0.04 (9.8) | 2.73 ± 0.03 (12.8) | 2.61 ± 0.12 (17.0) |
| 6 | 5c | 3.17 ± 0.01 (7.1) | 2.82 ± 0.04 (16.5) | 3.01 ± 0.02 (35.0) |
| 7 | 5d | 2.98 ± 0.03 (0.7) | 3.26 ± 0.12 (34.7) | 2.66 ± 0.04 (19.3) |
| 8 | 5e | 3.03 ± 0.04 (2.4) | 3.00 ± 0.04 (24.0) | 2.91 ± 0.01 (30.5) |
| 9 | 5f | 2.99 ± 0.07 (1.0) | 2.78 ± 0.05 (14.9) | 2.57 ± 0.07 (15.2) |
| 10 | 5g | 3.11 ± 0.02 (5.1) | 3.09 ± 0.04 (27.7) | 2.87 ± 0.03 (28.7) |
| 11 | 5h | 3.00 ± 0.06 (1.4) | 2.73 ± 0.05 (12.8) | 2.69 ± 0.04 (20.6) |
| 12 | 5i | 3.31 ± 0.01 (11.8) | 3.20 ± 0.03 (32.2) | 3.35 ± 0.06 (51.1) |
| 13 | 5j | 3.08 ± 0.04 (4.1) | 2.96 ± 0.02 (22.3) | 2.79 ± 0.03 (25.1) |
| 14 | 7a | 3.48 ± 0.06 (17.7) | 4.77 ± 0.07 (97.1) | 4.34 ± 0.04 (94.6) |
| 15 | 7b | 3.12 ± 0.03 (5.4) | 4.21 ± 0.14 (74.0) | 3.98 ± 0.09 (78.5) |
| 16 | 7c | 3.00 ± 0.09 (1.4) | 3.83 ± 0.03 (58.3) | 3.42 ± 0.12 (53.4) |
| 17 | 7d | 2.98 ± 0.00 (0.7) | 3.61 ± 0.05 (49.2) | 2.85 ± 0.04 (27.8) |
| 18 | 7e | 3.39 ± 0.03 (14.5) | 4.31 ± 0.04 (78.1) | 4.57 ± 0.03 (104.9) |
| 19 | 7f | 3.02 ± 0.01 (2.0) | 3.98 ± 0.06 (64.5) | 3.88 ± 0.02 (74.0) |
| 20 | 7g | 3.14 ± 0.02 (6.1) | 3.29 ± 0.05 (36.0) | 3.10 ± 0.01 (39.0) |
| 21 | 7h | 3.19 ± 0.07 (7.8) | 3.83 ± 0.02 (58.3) | 3.62 ± 0.03 (62.3) |
| 22 | 7i | 3.20 ± 0.01 (8.1) | 4.51 ± 0.07 (86.4) | 4.24 ± 0.05 (90.1) |
| 23 | 7j | 3.37 ± 0.02 (13.9) | 3.89 ± 0.03 (60.7) | 3.67 ± 0.02 (64.6) |

| Entry | Compd. | After 90 min. | After 120 min. | Potency * |
|---|---|---|---|---|
| 1 | Control | 2.20 ± 0.03 (0) | 2.19 ± 0.02 (0) | — |
| 2 | Indomethacin | 3.29 ± 0.01 (49.5) | 3.43 ± 0.05 (56.6) | 100 |
| 3 | Ibuprofen | 3.09 ± 0.04 (40.5) | 3.29 ± 0.03 (50.2) | 89 |
| 4 | 5a | 2.84 ± 0.02 (29.1) | 2.84 ± 0.05 (29.7) | 52 |
| 5 | 5b | 2.66 ± 0.01 (20.9) | 2.67 ± 0.06 (21.9) | 39 |
| 6 | 5c | 2.65 ± 0.05 (20.5) | 2.63 ± 0.10 (20.1) | 36 |
| 7 | 5d | 2.49 ± 0.03 (13.2) | 2.37 ± 0.01 (8.2) | 14 |
| 8 | 5e | 2.98 ± 0.03 (35.5) | 3.25 ± 0.02 (48.4) | 86 |
| 9 | 5f | 2.77 ± 0.05 (25.9) | 3.26 ± 0.04 (48.9) | 86 |
| 10 | 5g | 2.29 ± 0.05 (4.1) | 2.27 ± 0.03 (3.7) | 7 |
| 11 | 5h | 2.41 ± 0.02 (9.5) | 2.33 ± 0.02 (6.4) | 11 |
| 12 | 5i | 3.55 ± 0.07 (61.4) | 2.48 ± 0.04 (13.2) | 23 |
| 13 | 5j | 3.20 ± 0.04 (45.5) | 3.20 ± 0.03 (46.1) | 81 |
| 14 | 7a | 4.10 ± 0.02 (86.4) | 3.98 ± 0.11 (81.7) | 144 |
| 15 | 7b | 3.85 ± 0.05 (75.0) | 3.52 ± 0.06 (60.7) | 107 |
| 16 | 7c | 3.36 ± 0.15 (52.7) | 3.33 ± 0.11 (52.1) | 92 |
| 17 | 7d | 2.53 ± 0.02 (15.0) | 2.46 ± 0.09 (12.3) | 22 |
| 18 | 7e | 5.20 ± 0.07 (136.4) | 5.35 ± 0.03 (144.3) | 255 |
| 19 | 7f | 3.88 ± 0.04 (76.4) | 5.79 ± 0.04 (164.4) | 290 |
| 20 | 7g | 3.16 ± 0.06 (43.6) | 3.92 ± 0.08 (79.0) | 140 |
| 21 | 7h | 3.49 ± 0.18 (58.6) | 3.30 ± 0.02 (50.7) | 90 |
| 22 | 7i | 4.35 ± 0.02 (97.7) | 4.85 ± 0.04 (121.5) | 215 |
| 23 | 7j | 3.84 ± 0.15 (74.5) | 4.92 ± 0.07 (124.7) | 220 |

* Relative to indomethacin at 120 min.

TABLE 5

COX-1/2 inhibitory properties of the tested compounds.

| Entry | Compd. | IC$_{50}$, μM ± SD COX-1 | IC$_{50}$, μM ± SD COX-2 | SI$_{(COX-2/COX-1)}$ |
|---|---|---|---|---|
| 1 | 1 (ibuprofen) | 10.89 ± 0.54 | 126.36 ± 8.94 | 11.6 |
| 2 | 7a | 2.70 ± 0.13 | 78.26 ± 5.54 | 29.0 |
| 3 | 7e | 13.25 ± 0.65 | 69.77 ± 4.93 | 5.3 |
| 4 | 7f | 4.86 ± 0.24 | 141.10 ± 11.08 | 29.0 |
| 5 | 7g | 2.65 ± 0.13 | 144.02 ± 11.19 | 54.3 |
| 6 | 7h | 10.37 ± 0.51 | 132.85 ± 9.40 | 12.8 |
| 7 | 7j | 8.29 ± 0.41 | 116.35 ± 8.23 | 14.0 |

Example 8: Molecular Modeling Studies—2D-QSAR Study

Materials and Methods

Figure 4:
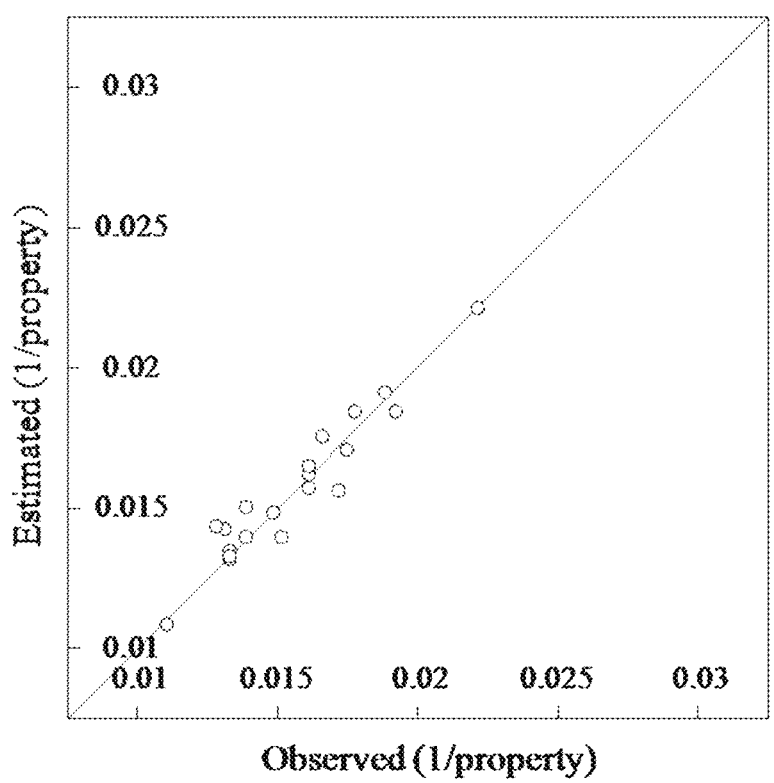
FIG. 4 is a 2D-QSAR model plot of correlations representing the Estimated (1/property) versus observed (1/property) anti-inflammatory properties of the synthesized conjugates.

Three descriptor 2D-quantitative structure-activity relationship (QSAR) model ($R^2$=0.917) describes the anti-inflammatory properties of the synthesized conjugates covering the anti-inflammatory range=45-90, 45-93 for the observed and predicted property (% inhibition of edema thickness at 3 h effect) (Tables 6,7; FIG. 4). The maximum atomic state energy for atom C (atomic type descriptor) is the first descriptor of QSAR model based on the t-criterion value=12.150. Minimum resonance energy for bond H—C (semi-empirical descriptor), positively participates in the QSAR model describing the 1/property of the anti-inflammatory active conjugates. In other words, the high value of this descriptor estimates the low property of the tested conjugate and vice versa. This is obvious due to the descriptor values for conjugates 7f and 5i=10.2574, 10.3591, respectively estimating property=93, 45, respectively (Supplementary Table 51). Resonance energy between given two atomic species can be calculated by Equation (1) (Katritzky, A. R. et al., *CODESSA-Pro Software Manual* 2005, 74-75).

$$E_R(AB) = \Sigma_{\mu \in A} \Sigma_{\nu \in B} P_{\mu\nu} \beta_{\mu\nu} \quad \text{(Equation 1)}$$

Where, A and B are two given atomic species. $P_{\mu\nu}$ is the density matrix elements over atomic basis $\{\mu\nu\}$. $\beta_{\mu\nu}$ is the resonance integrals on atomic basis $\{\mu\nu\}$.

Minimum coulombic interaction for bond C—O (semi-empirical descriptor) negatively participates in the QSAR model (coefficient=−0.0175012). This explains the controlled influence on the estimated property values for the highest and lowest anti-inflammatory conjugates 7f and 5i (descriptor values=8.1657, 8.1406, respectively). Total interaction energy between two given atomic species can be calculated by Equation (2) (Katritzky, A. R. et al., *CODESSA-Pro Software Manual* 2005, 74-75).

$$E_{tot}(AB) = E_C(AB) E_{exc}(AB) \quad \text{(Equation 2)}$$

Where, A and B stands for two atomic species. $E_C(AB)$ is the electrostatic interaction energy between two atomic species. $E_{exc}(AB)$ is the electronic exchange energy between two atomic species.

Validation of the attained QSAR model is supported by the statistical parameters observed for correlation coefficient ($R^2$=0.917, $R^2$cvOO=0.881, $R^2$cvMO=0.883) in addition to the Fisher criteria (F=58.647) and standard deviation ($s^2$=7.137e-007). The compatible estimated properties relative to the experimentally observed as supported the QSAR model (Table 7).

TABLE 6

Descriptors of the BMLR-QSAR model for the tested anti-inflammatory active agents.

| Entry | ID | Coefficient | s | T | Descriptor |
|---|---|---|---|---|---|
| 1 | 0 | −2.44342 | 0.213 | −11.484 | Intercept |
| 2 | $D_1$ | 0.0220937 | 0.002 | 12.150 | Max. atomic state energy for atom C |
| 3 | $D_2$ | 0.0303895 | 0.005 | 6.130 | Min. resonance energy for bond H—C |
| 4 | $D_3$ | −0.0175012 | 0.003 | −6.656 | Min. coulombic interaction for bond C—O |

N = 20,
n = 3,
$R^2$ = 0.917,
$R^2$cvOO = 0.881,
$R^2$cvMO = 0.883,
F = 58.647,
$s^2$ = 7.137e-007
log(1/property) = −2.44342 + (0.0220937 × $D_1$) + (0.0303895 × $D_2$) − (0.0175012 × $D_3$)

TABLE 7

Observed and estimated anti-inflammatory properties for the tested compounds according to the BMLR-QSAR model.

| Entry | Compound | Observed (1/property) | Observed property | Estimated (1/property) | Estimated property |
|---|---|---|---|---|---|
| 1 | 5a | 0.013889 | 72 | 0.013872 | 72 |
| 2 | 5b | 0.019231 | 52 | 0.018355 | 54 |
| 3 | 5c | 0.018868 | 53 | 0.019049 | 52 |
| 4 | 5d | 0.016667 | 60 | 0.017544 | 57 |
| 5 | 5e | 0.016129 | 62 | 0.016202 | 62 |
| 6 | 5f | 0.016129 | 62 | 0.016425 | 61 |
| 7 | 5g | 0.017241 | 58 | 0.015585 | 64 |
| 8 | 5h | 0.017544 | 57 | 0.016984 | 59 |
| 9 | 5i | 0.022222 | 45 | 0.022088 | 45 |
| 10 | 5j | 0.013889 | 72 | 0.014943 | 67 |
| 11 | 7a | 0.013158 | 76 | 0.014253 | 70 |
| 12 | 7b | 0.016129 | 62 | 0.015629 | 64 |
| 13 | 7c | 0.014925 | 67 | 0.014787 | 68 |
| 14 | 7d | 0.015152 | 66 | 0.013894 | 72 |
| 15 | 7e | 0.013333 | 75 | 0.013181 | 76 |
| 16 | 7f | 0.011111 | 90 | 0.010787 | 93 |
| 17 | 7g | 0.013333 | 75 | 0.013469 | 74 |
| 18 | 7h | 0.013333 | 75 | 0.013267 | 75 |
| 19 | 7i | 0.017857 | 56 | 0.018378 | 54 |
| 20 | 7j | 0.012821 | 78 | 0.014268 | 70 |

Example 9: Molecular Modeling Studies—3D-Pharmacophore Study 3D-pharmacophore study (Discovery Studio 2.5 software) exhibits three features that govern the biological properties (2 hydrophobics "H-1, H-2" and one hydrogen bonding donor "HBD"). All the synthesized conjugates (compound 7e is an exception) have the same alignment in the generated 3D-pharmacophore model. The phenyl ring and alkyl group of ibuprofen are aligned in H-1 and H-2, respectively. This confirms that the anti-inflammatory properties revealed are still controlled by this residue. The amidic nitrogen due to conjugation of amino acid with the ibuprofen carboxylic group is aligned with the HBD confirming the effect of amino acid derivative used in the biological properties exhibited. Compound 7e shows a slightly different alignment in the 3D-Pharmacophore. Where the phenyl group of amino acid is aligned in H-1 and amidic nitrogen due to the conjugation of the amino acid with p-aminophenol is aligned in HBD. The estimated biological properties due to 3D-pharmacophoric modeling are correlated with the experimental values preserving the potencies of the synthesized conjugates among each other (Table 8).

TABLE 8

Fit values and estimated activity values of the tested anti-inflammatory active conjugates according to the 3D-pharmacophore modeling.

| Entry | Compound | Observed property | Estimated property | Fit value |
|---|---|---|---|---|
| 1 | 5a | 72 | 68 | 5.740 |
| 2 | 5b | 52 | 63 | 5.776 |
| 3 | 5c | 53 | 68 | 5.745 |
| 4 | 5d | 60 | 68 | 5.741 |
| 5 | 5e | 62 | 66 | 5.757 |
| 6 | 5f | 62 | 71 | 5.726 |
| 7 | 5g | 58 | 60 | 5.794 |
| 8 | 5h | 57 | 62 | 5.780 |
| 9 | 5i | 45 | 55 | 5.835 |
| 10 | 5j | 72 | 74 | 5.705 |
| 11 | 7a | 76 | 63 | 5.777 |
| 12 | 7b | 62 | 71 | 5.723 |
| 13 | 7c | 67 | 55 | 5.833 |
| 14 | 7d | 66 | 70 | 5.733 |
| 15 | 7e | 75 | 72 | 5.717 |
| 16 | 7f | 90 | 77 | 5.689 |
| 17 | 7g | 75 | 65 | 5.763 |

TABLE 8-continued

Fit values and estimated activity values of the tested anti-inflammatory active conjugates according to the 3D-pharmacophore modeling.

| Entry | Compound | Observed property | Estimated property | Fit value |
|---|---|---|---|---|
| 18 | 7h | 75 | 71 | 5.723 |
| 19 | 7i | 56 | 63 | 5.772 |
| 20 | 7j | 78 | 62 | 5.783 |

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

I claim:

1. An ibuprofen hybrid conjugate comprising the general formula (i)

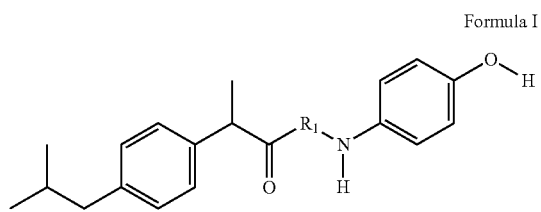

Formula I wherein, $R_1$ is independently H, alkyl, alkenyl, alkynyl, alkoxy, cycloalkyl, aryl, heteroaryl, wherein each of which is unsubstituted or substituted with H, OH, halogen, alkyl, aryl, —COOH, —COOR$_2$, CH$_2$OH, —CH$_2$OR$_2$, —COSR$_2$, —CONH$_2$, —CH$_2$NH$_2$, CH$_2$NHR$_3$, —CH$_2$NR$_3$R$_4$, —NCO, —CH$_2$-halogen, —CHO, —CN, —CONH—CO—R$_2$, —CH$_2$O—CO—O—R$_2$; NO$_2$, NH$_2$, NHR$_3$, NR$_3$R$_4$, —S—;

$R_2$ is independently H, halogen, alkyl, aryl, heteroaryl; and $R_3$ and $R_4$ are independently H, halogen, alkyl, aryl, heteroaryl;

or an enantiomer, tautomer, stereoisomers, solvate, zwitterion, polymorph, prodrug, or a pharmaceutically acceptable salt thereof.

2. The ibuprofen hybrid conjugate of claim 1, wherein $R_1$ is H.

3. The ibuprofen hybrid conjugate of claim 1, wherein $R_1$ is alkyl.

4. The ibuprofen hybrid conjugate of claim 1, wherein $R_1$ is alkyl substituted with aryl.

5. An ibuprofen hybrid conjugate comprising the structure of any of the following compounds:

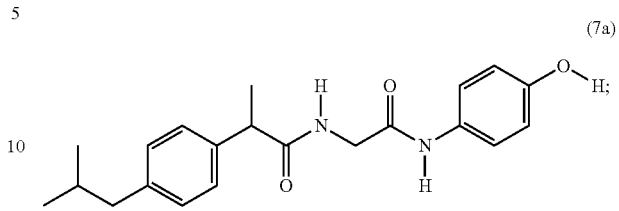
(7a)

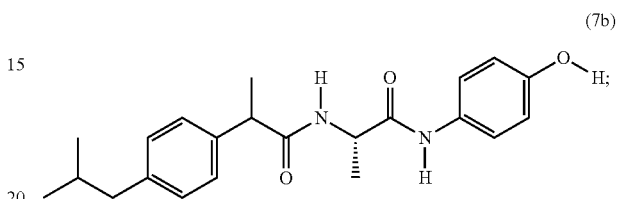
(7b)

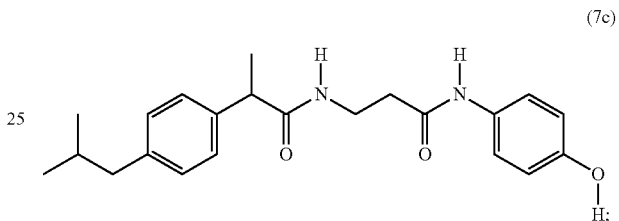
(7c)

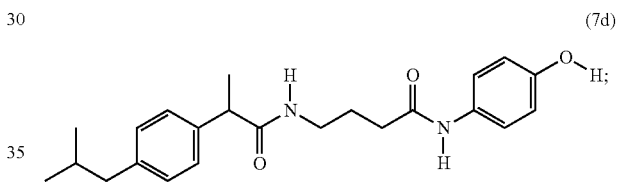
(7d)

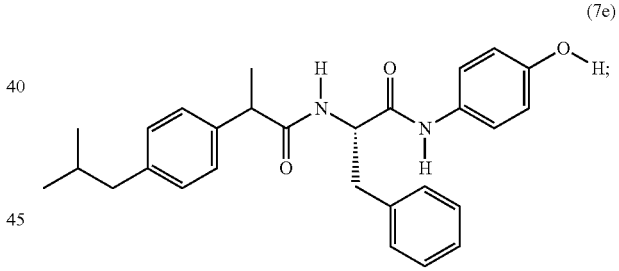
(7e)

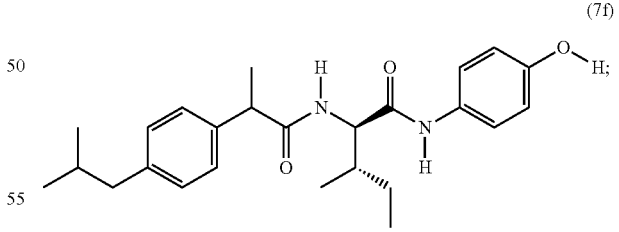
(7f)

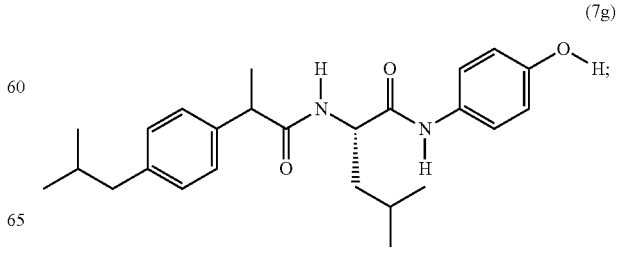
(7g)

-continued

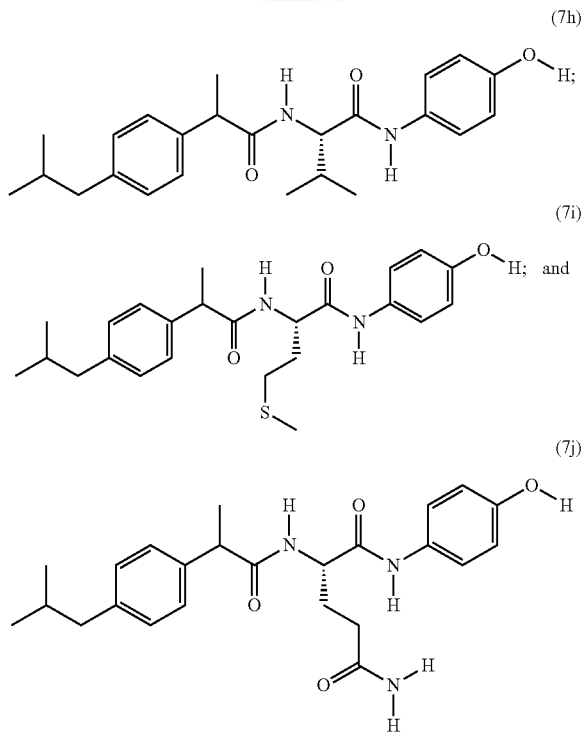

or a pharmaceutically acceptable salt thereof.

6. A pharmaceutical composition comprising an effective amount of at least one of the ibuprofen hybrid conjugates of claim 5, or a pharmaceutically acceptable salt thereof and a pharmaceutically acceptable excipient.

7. The pharmaceutical composition of claim 6, wherein the composition is formulated for oral administration.

8. The pharmaceutical composition of claim 6, wherein the composition is formulated for parenteral administered composition.

9. A method of treating inflammation in a subject in need thereof, comprising administering to the subject the pharmaceutical composition according to claim 6 in an amount effective to reduce inflammation.

10. The method of claim 9, wherein the pharmaceutical composition reduces or eliminate one or more symptoms of inflammation.

11. The method of claim 9, wherein the one or more symptoms of inflammation are selected from the group consisting of tissue heat, pain, redness, swelling, or loss of function.

12. A method of reducing pain in a subject in need thereof comprising, administering to the subject the pharmaceutical composition according to claim 6 in an amount effective to reduce pain.

13. The method of claim 12, wherein the pain is caused by appendicitis, arthritis, bone fracture or break, burns, cancer, central pain, congenital conditions such as curvature of the spine, chronic or acute pain, cluster headaches, crash injury, dental pain, fibromyalgia, gallbladder disease, gastrointestinal disorders, headaches, herpes neuralgia, improper lifting techniques, infection, inflammatory disease, joint damage, lower back pain, menstruation, migraines, multiple sclerosis, nerve damage, neuropathic pain, a non-inflammatory neuropathic or dysfunctional pain condition, nociceptive pain, opioid resistant pain, osteoarthritis, pain during labor and delivery, pain syndromes, phantom limb pain, poor posture, post-operative pain, rheumatoid arthritis, sprains, spinal cord injury, strains, surgery, trauma, toothache, visceral pain, or wound cleansing and debridement.

14. The method of claim 12, wherein the subject is a human.

15. A method reducing or eliminating fever in a subject in need thereof comprising, administering to the subject the pharmaceutical composition according to claim 6 in an amount effective to reduce fever.

* * * * *